United States Patent
Fritsch et al.

(10) Patent No.: US 7,584,103 B2
(45) Date of Patent: Sep. 1, 2009

(54) AUTOMATED EXTRACTION OF SEMANTIC CONTENT AND GENERATION OF A STRUCTURED DOCUMENT FROM SPEECH

(75) Inventors: Juergen Fritsch, Pittsburgh, PA (US); Michael Finke, Pittsburgh, PA (US); Detlef Koll, Pittsburgh, PA (US); Monika Woszczyna, Pittsburgh, PA (US); Girija Yegnanarayanan, Bedford, MA (US)

(73) Assignee: Multimodal Technologies, Inc., Pittsburgh, PA (US)

( * ) Notice: Subject to any disclaimer, the term of this patent is extended or adjusted under 35 U.S.C. 154(b) by 888 days.

(21) Appl. No.: 10/923,517

(22) Filed: Aug. 20, 2004

(65) Prior Publication Data
US 2006/0041428 A1 Feb. 23, 2006

(51) Int. Cl.
*G10L 15/18* (2006.01)
(52) U.S. Cl. .................... 704/257; 704/260
(58) Field of Classification Search .............. 704/235, 704/9, 257, 260, 266
See application file for complete search history.

(56) References Cited

U.S. PATENT DOCUMENTS

| | | | |
|---|---|---|---|
| 5,384,892 A | 1/1995 | Strong | |
| 5,434,962 A | 7/1995 | Kyojima et al. | |
| 5,669,007 A | 9/1997 | Tateishi | |
| 5,797,123 A | 8/1998 | Chou et al. | |
| 5,809,476 A | 9/1998 | Ryan | |
| 5,839,106 A | 11/1998 | Bellegarda | |
| 5,926,784 A | 7/1999 | Richardson et al. | |
| 5,970,449 A | 10/1999 | Alleva et al. | |
| 6,041,292 A | 3/2000 | Jochim | |
| 6,055,494 A | 4/2000 | Friedman | |
| 6,112,168 A | 8/2000 | Corston et al. | |
| 6,122,613 A | 9/2000 | Baker | |
| 6,122,614 A | 9/2000 | Kahn et al. | |
| 6,154,722 A | 11/2000 | Bellegarda | |
| 6,182,029 B1 | 1/2001 | Friedman | |

(Continued)

FOREIGN PATENT DOCUMENTS

EP 0903727 A1 3/1999

(Continued)

OTHER PUBLICATIONS

Rosenthal et al., "Voice-Enabled, Structured Medical Reporting," IEEE Intelligent Systems, vol. 13, No. 1, Jan. 1, 1998, pp. 70-73.

*Primary Examiner*—Angela A Armstrong
(74) *Attorney, Agent, or Firm*—Robert Plotkin, P.C.

(57) ABSTRACT

Techniques are disclosed for automatically generating structured documents based on speech, including identification of relevant concepts and their interpretation. In one embodiment, a structured document generator uses an integrated process to generate a structured textual document (such as a structured textual medical report) based on a spoken audio stream. The spoken audio stream may be recognized using a language model which includes a plurality of sub-models arranged in a hierarchical structure. Each of the sub-models may correspond to a concept that is expected to appear in the spoken audio stream. Different portions of the spoken audio stream may be recognized using different sub-models. The resulting structured textual document may have a hierarchical structure that corresponds to the hierarchical structure of the language sub-models that were used to generate the structured textual document.

21 Claims, 22 Drawing Sheets

U.S. PATENT DOCUMENTS

| | | | |
|---|---|---|---|
| 6,243,669 | B1 | 6/2001 | Horiguchi et al. |
| 6,249,765 | B1 | 6/2001 | Adler et al. |
| 6,278,968 | B1 | 8/2001 | Franz et al. |
| 6,292,771 | B1 | 9/2001 | Haug et al. |
| 6,304,848 | B1 | 10/2001 | Singer |
| 6,304,870 | B1 | 10/2001 | Kushmerick et al. |
| 6,405,165 | B1 | 6/2002 | Blum et al. |
| 6,434,547 | B1 * | 8/2002 | Mishelevich et al. ............ 707/3 |
| 6,490,561 | B1 | 12/2002 | Wilson et al. |
| 6,526,380 | B1 * | 2/2003 | Thelen et al. ................ 704/251 |
| 6,535,849 | B1 | 3/2003 | Pakhomov et al. |
| 6,556,964 | B2 | 4/2003 | Haug et al. |
| 6,609,087 | B1 | 8/2003 | Miller et al. |
| 6,684,188 | B1 * | 1/2004 | Mitchell et al. ................ 705/3 |
| 6,754,626 | B2 * | 6/2004 | Epstein ....................... 704/235 |
| 6,766,328 | B2 | 7/2004 | Stefanchik et al. |
| 6,915,254 | B1 | 7/2005 | Heinze et al. |
| 7,028,038 | B1 | 4/2006 | Pakhomov |
| 7,043,426 | B2 | 5/2006 | Roberge et al. |
| 2002/0087311 | A1 | 7/2002 | Leung Lee et al. |
| 2002/0087315 | A1 | 7/2002 | Lee |
| 2002/0123891 | A1 | 9/2002 | Epstein |
| 2002/0128816 | A1 | 9/2002 | Haug et al. |
| 2002/0156817 | A1 | 10/2002 | Lemus |
| 2003/0093272 | A1 | 5/2003 | Soufflet et al. |
| 2003/0105638 | A1 | 6/2003 | Taira |
| 2003/0144885 | A1 | 7/2003 | Sachdev |
| 2003/0167266 | A1 | 9/2003 | Saldanha et al. |
| 2004/0030704 | A1 | 2/2004 | Stefanchik et al. |
| 2004/0172237 | A1 | 9/2004 | Saldanha et al. |
| 2004/0172245 | A1 | 9/2004 | Rosen et al. |
| 2004/0243545 | A1 | 12/2004 | Boone et al. |
| 2004/0267574 | A1 | 12/2004 | Stefanchik et al. |
| 2005/0108010 | A1 | 5/2005 | Frankel et al. |
| 2005/0144184 | A1 | 6/2005 | Carus et al. |
| 2005/0273365 | A1 | 12/2005 | Baumgartner et al. |
| 2006/0190263 | A1 | 8/2006 | Finke et al. |

FOREIGN PATENT DOCUMENTS

| | | | |
|---|---|---|---|
| JP | 62221775 | A2 | 9/1987 |
| JP | 04175966 | A2 | 6/1992 |
| JP | 06168267 | A2 | 6/1994 |
| JP | 2000259175 | A2 | 9/2000 |
| JP | 2003022091 | A | 7/2001 |
| WO | WO 94/16434 | | 7/1994 |
| WO | WO 0054180 | A1 | 9/2000 |
| WO | 0058945 | A1 | 10/2000 |
| WO | WO 0141126 | A1 | 6/2001 |
| WO | 0233691 | A1 | 4/2002 |
| WO | WO 02/054033 | A3 | 7/2002 |
| WO | WO 02/054385 | A1 | 7/2002 |
| WO | WO 02/071391 | * | 9/2002 |
| WO | WO 02/071391 | A2 | 9/2002 |
| WO | WO 02/071391 | A3 | 9/2002 |

* cited by examiner

| | |
|---|---|
| 120 — GENERAL HOSPITAL | 118 — Date: 10/01/1993 |
| 114 — Patient Name: JANE DOE | |
| 116 — Chart #: 851D | |

S: Ms. XXXX comes in today complaining of a right watery and itchy eye. The patient states that it has been going on for several months now...

124 — PMHx: Significant for hysterectomy, BSO....
126 — Meds: Estratest 1 mg q.d.
128 — Allergies: NKDA.
130 — FamHx: Reviewed.
132 — SocHx: Reviewed.

O: WT. 140 T: 87.6 P: 84 BP: 116/64. GENERAL - The patient is a WDWN white female sitting up in no acute distress...

A: 1. Conjunctivitis, right eye. Suspect allergy, glaucoma cannot be ruled out.

P: 1. The patient is placed on BrandName eyedrops to put two drops in right eye three times a day.
2. The patient also is scheduled an appointment with Dr. Dyer, her optometrist for evaluation of her right eye to rule out possibility of glaucoma.
3. The patient will return if symptoms do not improve. Otherwise, patient will return on next regularly scheduled visit.

CT scan of the chest without contrast april twenty second two thousand three comparison to prior studies from march twenty six two thousand two and april six two thousand one paragraph technique %colon% helical five mm images from the apices through the adrenals %comma% reconstructed with lung and soft tissue algorithm %period% findings is patient is status post wedge resections of the anterior right upper lobe as well as of the posterior right lower lobe %period% there is no growth along suture lines %period% there are no new masses or nodules %period% there is no mediastinal adenopathy %period% there are no pleural nor pericardial effusions %period% there is minimal bilateral dependent atelectasis %period% %newparagraph% conclusion expected postoperative changes secondary to wedge resections of the right upper lobe and right lower lobe %comma% unchanged from the prior CT scan of march twenty sixth two thousand two %period% ICD9 two one two point three

FIG. 4

| | |
|---|---|
| CT scan of the chest | 22-APR-2003 |
| Comparison:<br>Prior studies from 26-MAR-2002 and 06-APR-2001 | |
| Technique:<br>Helical 5mm images from the apices through the adrenals, reconstructed with lung and soft tissue algorithm. | |
| Findings:<br>Patient is status post wedge resections of the anterior right upper lobe as well as of the posterior right lower lobe. There is no growth along suture lines. There are no new masses or nodules. There is no mediastinal adenopathy. There are no pleural nor pericardial effusions. There is minimal bilateral dependent atelectasis. | |
| Impression:<br>Expected postoperative changes secondary to wedge resections of the right upper lobe and right lower lobe, unchanged from the prior CT scan of 26-MAR-2002.<br>ICD9 212.3 | |

AUTOMATED EXTRACTION OF SEMANTIC CONTENT AND GENERATION OF A STRUCTURED DOCUMENT FROM SPEECH

CROSS REFERENCE TO RELATED APPLICATIONS

This application is related to a concurrently-filed U.S. Patent Application entitled "Document Transcription System Training," which is hereby incorporated by reference.

BACKGROUND

1. Field of the Invention

The present invention relates to automatic speech recognition and, more particularly, to techniques for automatically transcribing speech.

2. Related Art

It is desirable in many contexts to generate a written document based on human speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals. Transcripts in these and other fields typically need to be highly accurate (as measured in terms of the degree of correspondence between the semantic content (meaning) of the original speech and the semantic content of the resulting transcript) because of the reliance placed on the resulting transcripts and the harm that could result from an inaccuracy (such as providing an incorrect prescription drug to a patient). High degrees of reliability may, however, be difficult to obtain consistently for a variety of reasons, such as variations in: (1) features of the speakers whose speech is transcribed (e.g., accent, volume, dialect, speed); (2) external conditions (e.g., background noise); (3) the transcriptionist or transcription system (e.g., imperfect hearing or audio capture capabilities, imperfect understanding of language); or (4) the recording/transmission medium (e.g., paper, analog audio tape, analog telephone network, compression algorithms applied in digital telephone networks, and noises/artifacts due to cell phone channels).

At first, transcription was performed solely by human transcriptionists who would listen to speech, either in real-time (i.e., in person by "taking dictation") or by listening to a recording. One benefit of human transcriptionists is that they may have domain-specific knowledge, such as knowledge of medicine and medical terminology, which enables them to interpret ambiguities in speech and thereby to improve transcript accuracy. Human transcriptionists, however, have a variety of disadvantages. For example, human transcriptionists produce transcripts relatively slowly and are subject to decreasing accuracy over time as a result of fatigue.

Various automated speech recognition systems exist for recognizing human speech generally and for transcribing speech in particular. Speech recognition systems which create transcripts are referred to herein as "automated transcription systems" or "automated dictation systems." Off-the-shelf dictation software, for example, may be used by personal computer users to dictate documents in a word processor as an alternative to typing such documents using a keyboard.

Automated dictation systems typically attempt to produce a word-for-word transcript of speech. Such a transcript, in which there is a one-to-one mapping between words in the spoken audio stream and words in the transcript, is referred to herein as a "verbatim transcript." Automated dictation systems are not perfect and may therefore fail to produce perfect verbatim transcripts.

In some circumstances, however, a verbatim transcript is not desired. In fact, transcriptionists may intentionally introduce a variety of changes into the written transcription. A transcriptionist may, for example, filter out spontaneous speech effects (e.g., pause fillers, hesitations, and false starts), discard irrelevant remarks and comments, convert data into a standard format, insert headings or other explanatory materials, or change the sequence of the speech to fit the structure of a written report.

In the medical domain, for example, spoken reports produced by doctors are frequently transcribed into written reports having standard formats. For example, referring to FIG. 1B, an example of a structured and formatted medical report 111 is shown. The report 111 includes a variety of sections 112-138 which appear in a predetermined sequence when the report 111 is displayed. In the particular example shown in FIG. 1B, the report includes a header section 112, a subjective section 122, an objective section 134, an assessment section 136, and a plan section 138. Sections may include text as well as sub-sections. For example, the header section 112 includes a hospital name section 120 (containing the text "General Hospital"), a patient name section 114 (containing the text "Jane Doe"), a chart number section 116 (containing the text "851D"), and a report date section 118 (containing text "10/1/1993").

Similarly, the subjective section 122 includes various subjective information about the patient, included both in text and in a medical history section 124, a medications section 126, an allergies section 128, a family history section 130, and a social history section 132. The objective section 134 includes various objective information about the patient, such as her weight and blood pressure. Although not illustrated in FIG. 1B, the information in the objective section may include sub-sections for containing the illustrated information. The assessment section 136 includes a textual assessment of the patient's condition, and the plan subsection 138 includes a textual description of a plan of treatment.

Note that information may appear in a different form in the report 111 from the form in which such information was spoken by the dictating doctor. For example, the date in the report date section 118 may have been spoken as "october first nineteen ninety three, "the first of october ninety three," or in some other form. The transcriptionist, however, transcribed such speech using the text "10/1/1993" in the report date section 118, perhaps because the hospital specified in the hospital section 120 requires that dates in written reports be expressed in such a format.

Similarly, information in the medical report 111 may not appear in the same sequence as in the original audio recording, due to the need to conform to a required report format or for some other reason. For example, the dictating physician may have dictated the objective section 134 first, followed by the subjective section 122, and then by the header 120. The written report 111, however, contains the header 120 first, followed by the subjective section 122, and then the objective section 134. Such a report structure may, for example, be required for medical reports in the hospital specified in the hospital section 120.

The beginning of the report 111 may have been generated based on a spoken audio stream such as the following: "this is doctor smith on uh the first of october um nineteen ninety three patient ID eighty five one d um next is the patient's family history which i have reviewed . . . ." It should be apparent that a verbatim transcript of this speech would be difficult to understand and would not be particularly useful.

Note, for example, that certain words, such as "next is a," do not appear in the written report 111. Similarly, pause-filling utterances such as "uh" do not appear in the written report 111. In addition, the written report 111 organizes the original speech into the predefined sections 112-140 by re-ordering the speech. As these examples illustrate, the written report 111 is not a verbatim transcript of the dictating physician's speech.

In summary, a report such as the report 111 may be more desirable than a verbatim transcript for a variety of reasons (e.g., because it organizes information in a way that facilitates understanding). It would, therefore, be desirable for an automatic transcription system to be capable of generating a structured report (rather than a verbatim transcript) based on unstructured speech.

Referring to FIG. 1A, a dataflow diagram is shown of a prior art system 100 for generating a structured document 110 based on a spoken audio stream 102. Such a system produces the structured textual document 110 from the spoken audio stream 102 using a two-step process: (1) an automatic speech recognizer 104 generates a verbatim transcript 106 based on the spoken audio stream 102; and (2) a natural language processor 108 identifies structure in the transcript 106 and thereby creates the structured document 110, which has the same content as the transcript 106, but which is organized into the structure (e.g., report format) identified by the natural language processor 108.

For example, some existing systems attempt to generate structured textual documents by: (1) analyzing the spoken audio stream 102 to identify and distinguish spoken content in the audio stream 102 from explicit or implicit structural hints in the audio stream 102; (2) converting the "content" portions of the spoken audio stream 102 into raw text; and (3) using the identified structural hints to convert the raw text into the structured report 110. Examples of explicit structural hints include formatting commands (e.g., "new paragraph," "new line," "next item") and paragraph identifiers (e.g., "findings," "impression," "conclusion"). Examples of implicit structural hints include long pauses that may denote paragraph boundaries, prosodic cues that indicate ends of enumerations, and the spoken content itself.

For various reasons described in more detail below, the structured document 110 produced by the system 100 may be sub-optimal. For example, the structured document 110 may contain incorrectly transcribed (i.e., misrecognized) words, the structure of the structured document 110 may fail to reflect the desired document structure, and content from the spoken audio stream 102 may be inserted into the wrong sub-structures (e.g., sections, paragraphs, or sentences) in the structured document.

Furthermore, in addition to or instead of generating the structured document 110 based on the spoken audio stream 102, it may be desirable to extract semantic content (such as information about medications, allergies, or previous illnesses of the patient described in the audio stream 102) from the spoken audio stream 102. Although such semantic content may be useful for generating the structured document 110, such content may also be useful for other purposes, such as populating a database of patient information that can be analyzed independently of the document 110. Prior art systems, such as the system 100 shown in FIG. 1, however, typically are designed to generate the structured document 110 based primarily or solely on syntactic information in the spoken audio stream 102. Such systems, therefore, are not useful for extracting semantic content.

What is needed, therefore, are improved techniques for generating structured documents based on spoken audio streams.

SUMMARY

Techniques are disclosed for automatically generating structured documents based on speech, including identification of relevant concepts and their interpretation. In one embodiment, a structured document generator uses an integrated process to generate a structured textual document (such as a structured textual medical report) based on a spoken audio stream. The spoken audio stream may be recognized using a language model which includes a plurality of sub-models arranged in a hierarchical structure. Each of the sub-models may correspond to a concept that is expected to appear in the spoken audio stream. For example, sub-models may correspond to document sections. Sub-models may, for example, be n-gram language models or context-free grammars. Different portions of the spoken audio stream may be recognized using different sub-models. The resulting structured textual document may have a hierarchical structure that corresponds to the hierarchical structure of the language sub-models that were used to generate the structured textual document.

For example, in one aspect of the present invention, a method is provided which includes steps of: (A) identifying a probabilistic language model including a plurality of probabilistic language models associated with a plurality of sub-structures of a document; and (B) using a speech recognition decoder to apply the probabilistic language model to a spoken audio stream to produce a document including content organized into the plurality of sub-structures, wherein the content in each of the plurality of sub-structures is produced by recognizing speech using the probabilistic language model associated with the sub-structure. Another aspect of the present invention is directed to the probabilistic language model identified in step (A).

In yet another aspect of the present invention, a data structure is provided which includes: a plurality of language models logically organized in a hierarchy, the plurality of language models including a first language model and a second language model; wherein the first language model is a parent of the second language model in the hierarchy; wherein the first language model is suitable for recognizing speech representing a first concept associated with a substructure of a document; and wherein the second language model is suitable for recognizing speech representing a second concept associated with a subset of the substructure of the document.

In a further aspect of the present invention, a method is provided which includes steps of: (A) identifying a probabilistic language model including a plurality of probabilistic language models associated with a plurality of concepts logically organized in a first hierarchy; (B) using a speech recognition decoder to apply the probabilistic language model to a spoken audio stream to produce a document including content organized into a plurality of sub-structures logically organized in a second hierarchy having a logical structure defined by a path through the first hierarchy.

Other features and advantages of various aspects and embodiments of the present invention will become apparent from the following description and from the claims.

BRIEF DESCRIPTION OF THE DRAWINGS

FIG. 1B illustrates a textual medical report generated based on a spoken report;

FIG. 4 illustrates an example of a spoken audio stream in one embodiment of the present invention;

FIG. 6 is an example of a rendered document that is rendered based on the structured textual document of FIG. 5 according to one embodiment of the present invention;

DETAILED DESCRIPTION

Figure 2:
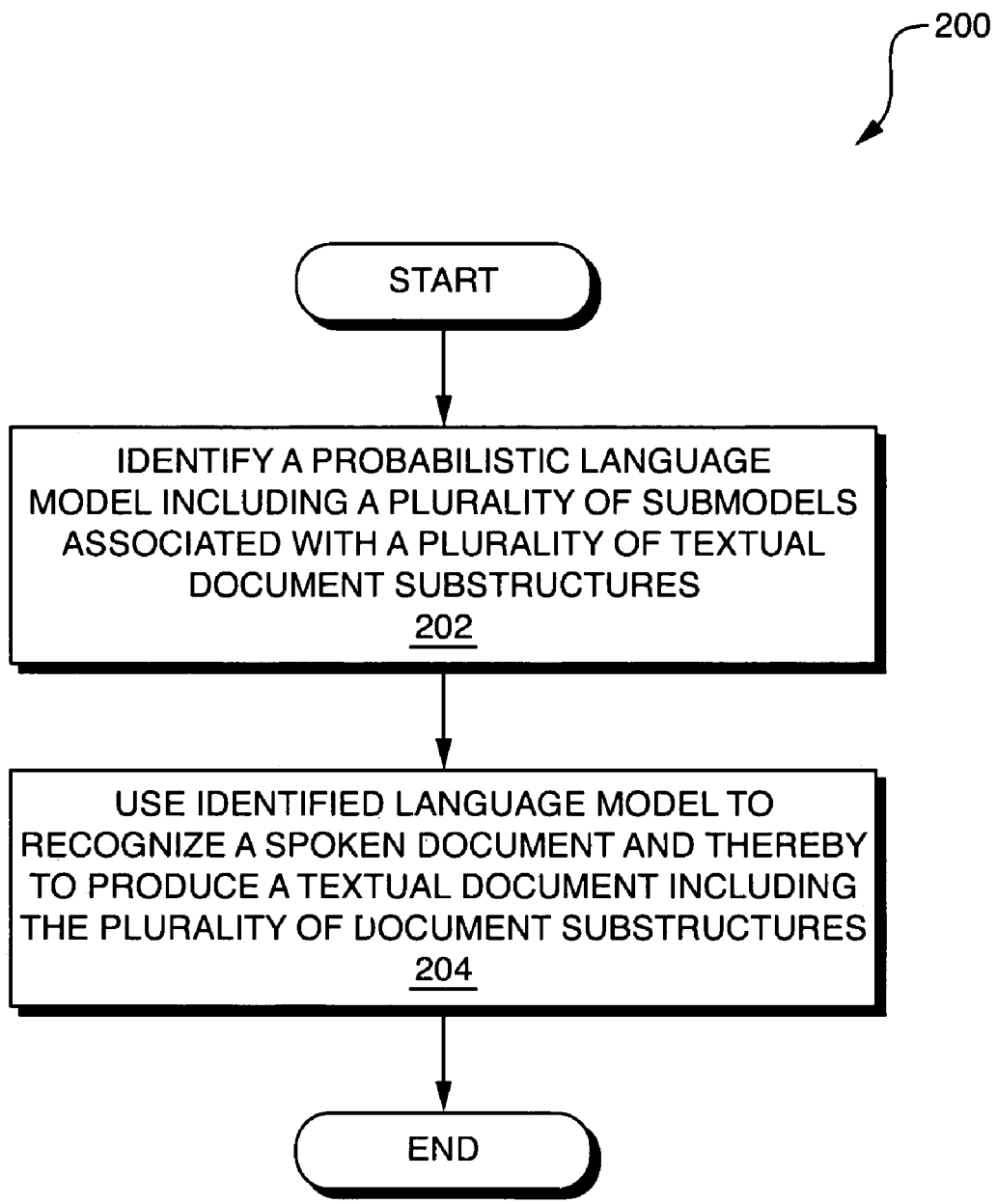
FIG. 2 is a flowchart of a method that is performed in one embodiment of the present invention to generate a structured textual document based on a spoken document.
Figure 3:
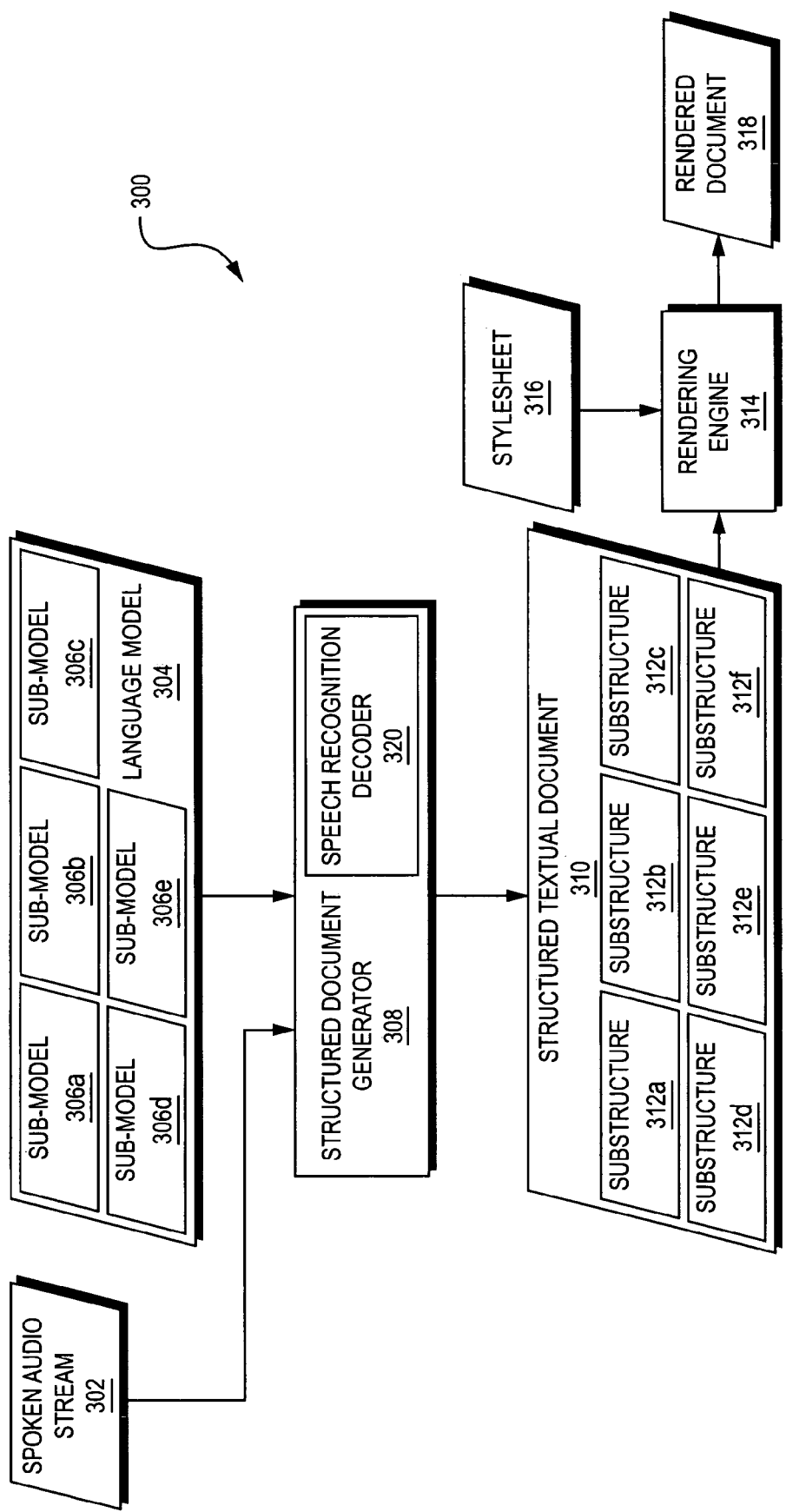
FIG. 3 is a dataflow diagram of a system that performs the method of FIG. 2 in one embodiment of the present invention.

Referring to FIG. 2, a flowchart is shown of a method 200 that is performed in one embodiment of the present invention to generate a structured textual document based on a spoken document. Referring to FIG. 3, a dataflow diagram is shown of a system 300 for performing the method 200 of FIG. 2 according to one embodiment of the present invention.

The system 300 includes a spoken audio stream 302, which may, for example, be a live or recorded spoken audio stream of a medical report dictated by a doctor. Referring to FIG. 4, a textual representation of an example of the spoken audio stream 302 is shown. In FIG. 4, text between percentage signs represents spoken punctuation (e.g., "% comma %", "% period %", and "% colon %") and explicit structural cues (e.g., "% new-paragraph %") in the audio stream 302. It may be seen from the audio stream 302 illustrated in FIG. 4 that a verbatim transcript of the audio stream 302 would not be particularly useful for purposes of understanding the diagnosis, prognosis, or other information contained in the medical report represented by the audio stream 302.

The system 300 also includes a probabilistic language model 304. The term "probabilistic language model" as used herein refers to any language model which assigns probabilities to sequences of spoken words. (Probabilistic) context-free grammars and n-gram language models 306a-e are both examples of "probabilistic language models" as that term is used herein.

In general, a context-free grammar specifies a plurality of spoken forms for a concept and associates probabilities with each of the spoken forms. A finite state grammar is an example of a context-free grammar. For example, a finite state grammar for the date Oct. 1, 1993, might include the spoken form "october first nineteen ninety three" with a probability of 0.7, the spoken form "ten one ninety three" with a probability of 0.2, and the spoken form "first october ninety three" with a probability of 0.1. The probability associated with each spoken form is an estimated probability that the concept will be spoken in that spoken form in a particular audio stream. A finite state grammar, therefore, is one kind of probabilistic language model.

In general, an n-gram language model specifies the probability that a particular sequence of n words will occur in a spoken audio stream. Consider, for example, a "unigram" language model, for which n=1. For each word in a language, a unigram specifies the probability that the word will occur in a spoken document. A "bigram" language model (for which n=2) specifies probabilities that pairs of words will occur in a spoken document. For example, a bigram model may specify the conditional probability that the word "cat" will occur in a spoken document given that the previous word in the document was "the". Similarly, a "trigram" language model specifies probabilities of three-word sequences, and so on. The probabilities specified by n-gram language models and finite state grammars may be obtained by training such documents using training speech and training text, as described in more detail in the above-referenced patent application entitled, "Document Transcription System Training."

The probabilistic language model 304 includes a plurality of sub-models 306a-e, each of which is a probabilistic language model. The sub-models 306a-e may include n-gram language models and/or finite state grammars in any combination. Furthermore, as described in more detail below, each of the sub-models 306a-e may contain further sub-models, and so on. Although five sub-models are shown in FIG. 3, the probabilistic language model 304 may include any number of sub-models.

The purpose of the system 300 shown in FIG. 3 is to produce a structured textual document 310 which includes content from the spoken audio stream 302, in which the content is organized into a particular structure, and where concepts are identified and interpreted in a machine-readable form. The structured textual document 310 includes a plurality of sub-structures 312a-f, such as sections, paragraphs, and/or sentences. Each of the sub-structures 312a-f may include further sub-structures, and so on. Although six sub-structures are shown in FIG. 3, the structured textual document 310 may include any number of sub-structures.

Figure 5:
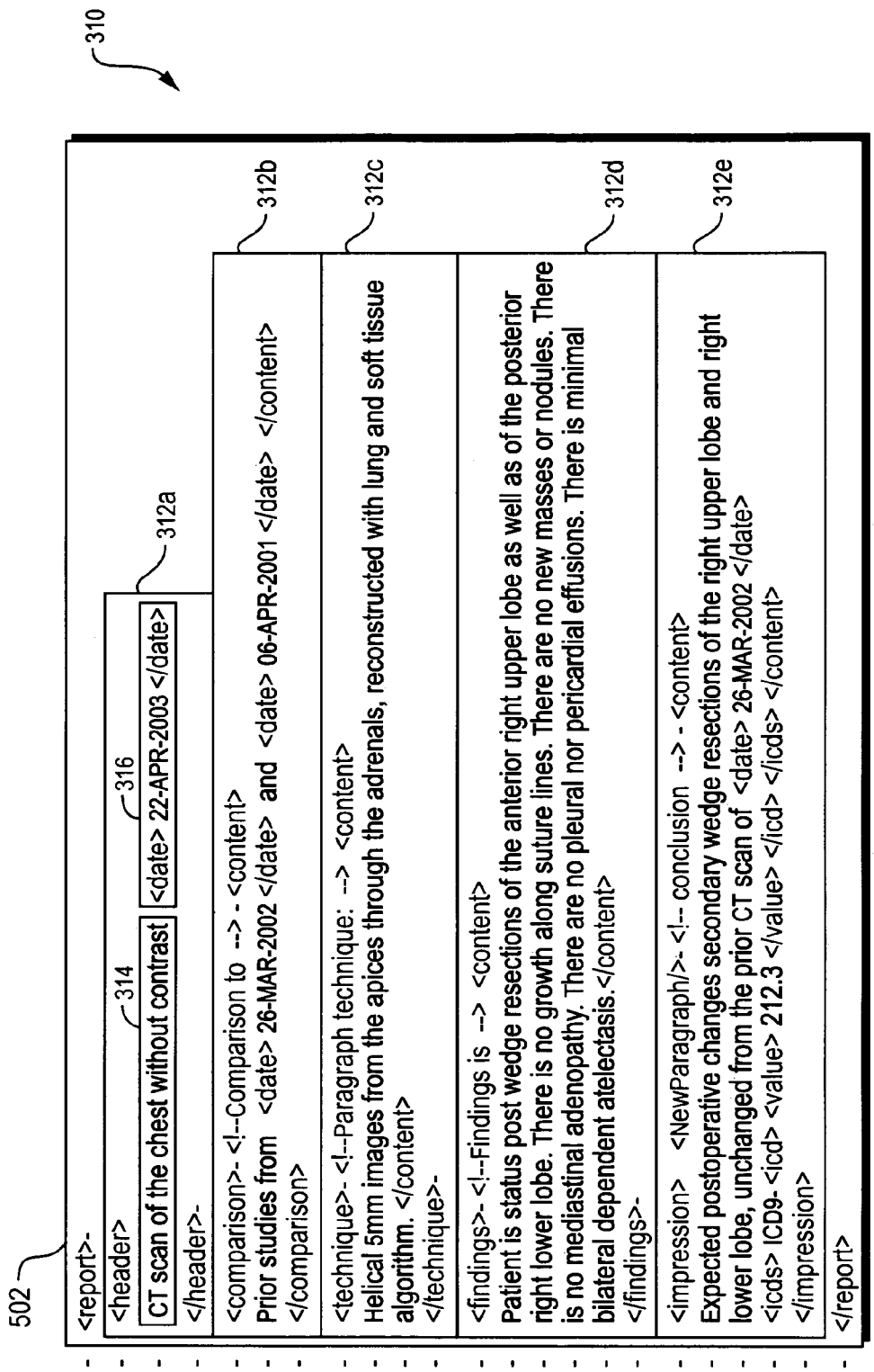
FIG. 5 illustrates a structured textual document according to one embodiment of the present invention.

For example, referring to FIG. 5, an example of the structured textual document 310 is shown. In the example illustrated in FIG. 5, the structured textual document 310 is an XML document. The structured textual document 310 may, however, be implemented in any form. As shown in FIG. 5, the structured document 310 includes six sub-structures 312a-f, each of which may represent a section of the document 310.

For example, the structured document 310 includes header section 312a which includes meta-data about the document 310, such as a title 314 of the document 310 ("CT scan of the chest without contrast") and the date 316 on which the document 310 was dictated ("<date>22-APR-2003</date>"). Note that the content in the header section 312a was obtained from the beginning of the spoken audio stream 302 (FIG. 4). Furthermore, note that the header section 312a includes both flat text (i.e., the title 314) and a sub-structure (e.g., the date 316) representing a concept that has been interpreted in a machine-readable form as a triplet of values (day-month-year).

Representing the date in a machine-readable form enables the date to be stored easily in a database and to be processed more easily than if the date were stored in a textual form. For example, if multiple dates in the audio stream 302 have been recognized and stored in machine-readable form, such dates may easily be compared to each other by a computer. As another example, statistical information about the content of the audio stream 302, such as the average time between doctor's visits, may easily be generated if dates are stored in computer-readable form. This advantage of embodiments of the present invention applies generally not only to dates but to the recognition of any kind of semantic content and the storage of such content in machine-readable form.

The structured document 310 further includes a comparison section 312b, which includes content describing prior studies performed on the same patient as the patient who is the subject of the document (report) 310. Note that the content in the comparison section 312b was obtained from the portion of the audio stream 302 beginning with "comparison to" and ending with "april six two thousand one", but that the comparison section 312b does not include the text "comparison to," which is an example of a section cue. The use of such cues to identify the beginning of a section or other document sub-structure will be described in more detail below.

In brief, the structured document 310 also includes a technique section 312c, which describes techniques that were performed in the procedures performed on the patient; a findings section 312d, which describes the doctor's findings; and an impression section 312e, which describes the doctor's impressions of the patient.

XML documents, such as the example structured document 310 illustrated in FIG. 5, typically are not intended for direct viewing by an end user. Rather, such documents typically are rendered in a form that is more easily readable before being presented to the end user. The system 300, for example, includes a rendering engine 314 which renders the structured textual document 310 based on a stylesheet 316 to produce a rendered document 318. Techniques for generating stylesheets and for rendering documents in accordance with stylesheets are well-known to those having ordinary skill in the art.

Referring to FIG. 6, an example of the rendered document 318 is shown. The rendered document 318 includes five sections 602a-e, each of which may correspond to one or more of the six sub-structures 312a-f in the structured textual document 310. More specifically, the rendered document 318 includes a header section 602a, a comparison section 602b, a technique section 602c, a findings section 602d, and an impression section 602e. Note that there may or may not be a one-to-one mapping between sections in the rendered document 318 and sub-structures in the structured textual document 310. For example, each of the sub-structures 312a-f need not represent a distinct type of document section. If, for example, two or more of the sub-structures 312a-f represent the same type of section (such as a header section), the rendering engine 314 may render both of the sub-structures in the same section of the rendered document 318.

The system 300 includes a structured document generator 308, which identifies the probabilistic language model 304 (step 202), and uses the language model 304 to recognize the spoken audio stream 302 and thereby to produce the structured textual document 310 (step 204). The structured document generator 308 may, for example, include an automatic speech recognition decoder 320 which produces each of the sub-structures 312a-f in the structured textual document 310 using a corresponding one of the sub-models 306a-e in the probabilistic language model 304. As is well-known to those having ordinary skill in the art, a decoder is a component of a speech recognizer which converts audio into text. The decoder 320 may, for example, produce sub-structure 312a by using sub-model 306a to recognize a first portion of the spoken audio stream 302. Similarly, the decoder 320 may produce sub-structure 312b by using sub-model 306b to recognize a second portion of the spoken audio stream 302.

Note that there need not be a one-to-one mapping between sub-models 306a-e in the language model 304 and sub-structures 312a-f in the structured document 310. For example, the speech recognition decoder may use the sub-model 306a to recognize a first portion of the spoken audio stream 302 and thereby produce sub-structure 312a, and use the same sub-model 306a to recognize a second portion of the spoken audio stream 302 and thereby produce sub-structure 312b. In such a case, multiple sub-structures in the structured textual document 310 may contain content for a single semantic structure (e.g., section or paragraph).

Sub-model 306a may, for example, be a "header" language model which is used to recognize portions of the spoken audio stream 302 containing content in the header section 312a; sub-model 306b may, for example, be a "comparison" language model which is used to recognize portions of the spoken audio stream 302 containing content in the comparison section 312b; and so on. Each such language model may be trained using training text from the corresponding section of training documents. For example, the header sub-model 306a may be trained using text from the header sections of a plurality of training documents, and the comparison sub-model may be trained using text from the comparison sections of the plurality of training documents.

Figure 7:
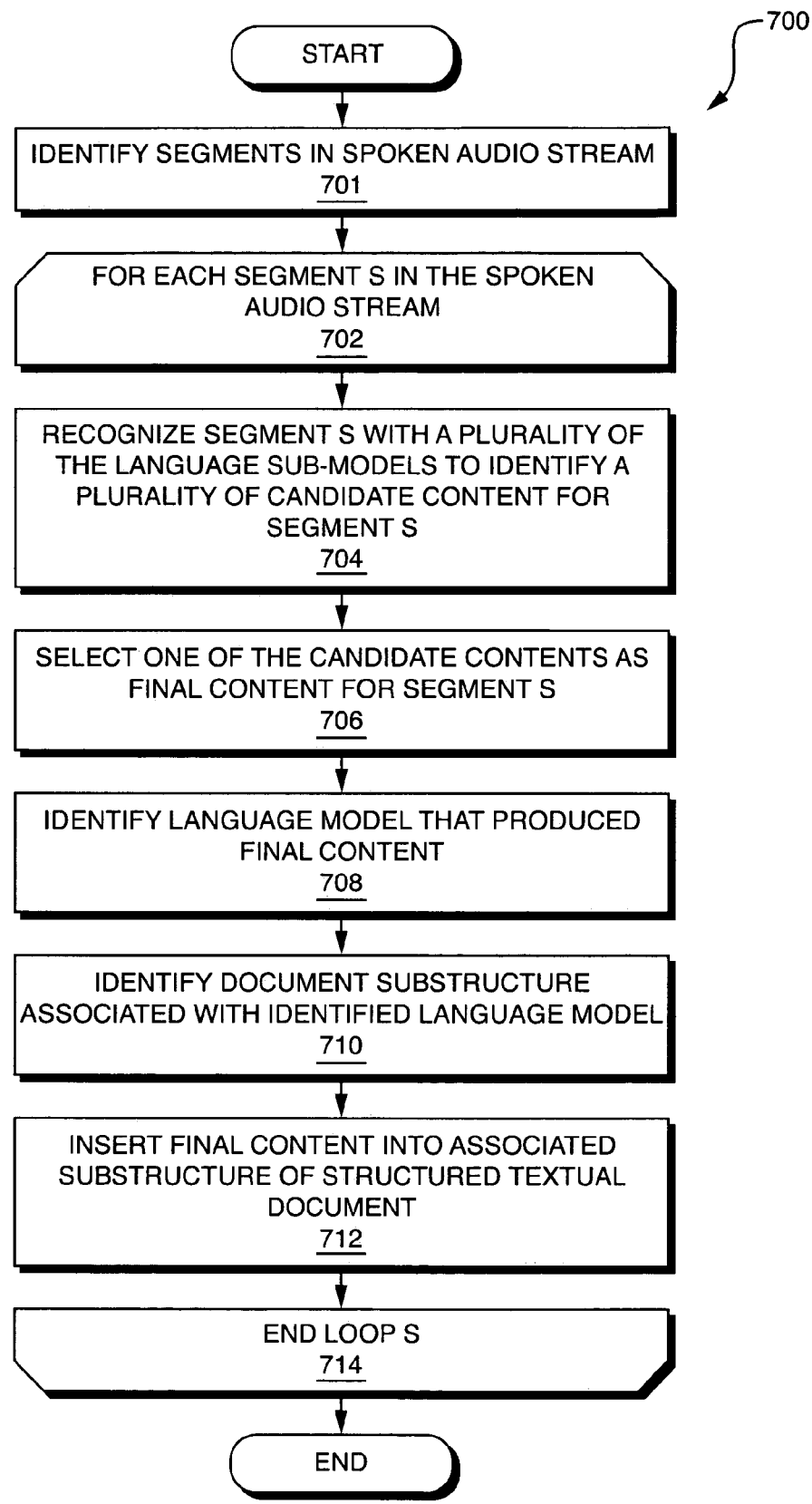
FIG. 7 is a flowchart of a method that is performed by the structured document generator of FIG. 3 in one embodiment of the present invention to generate a structured textual document.
Figure 8:
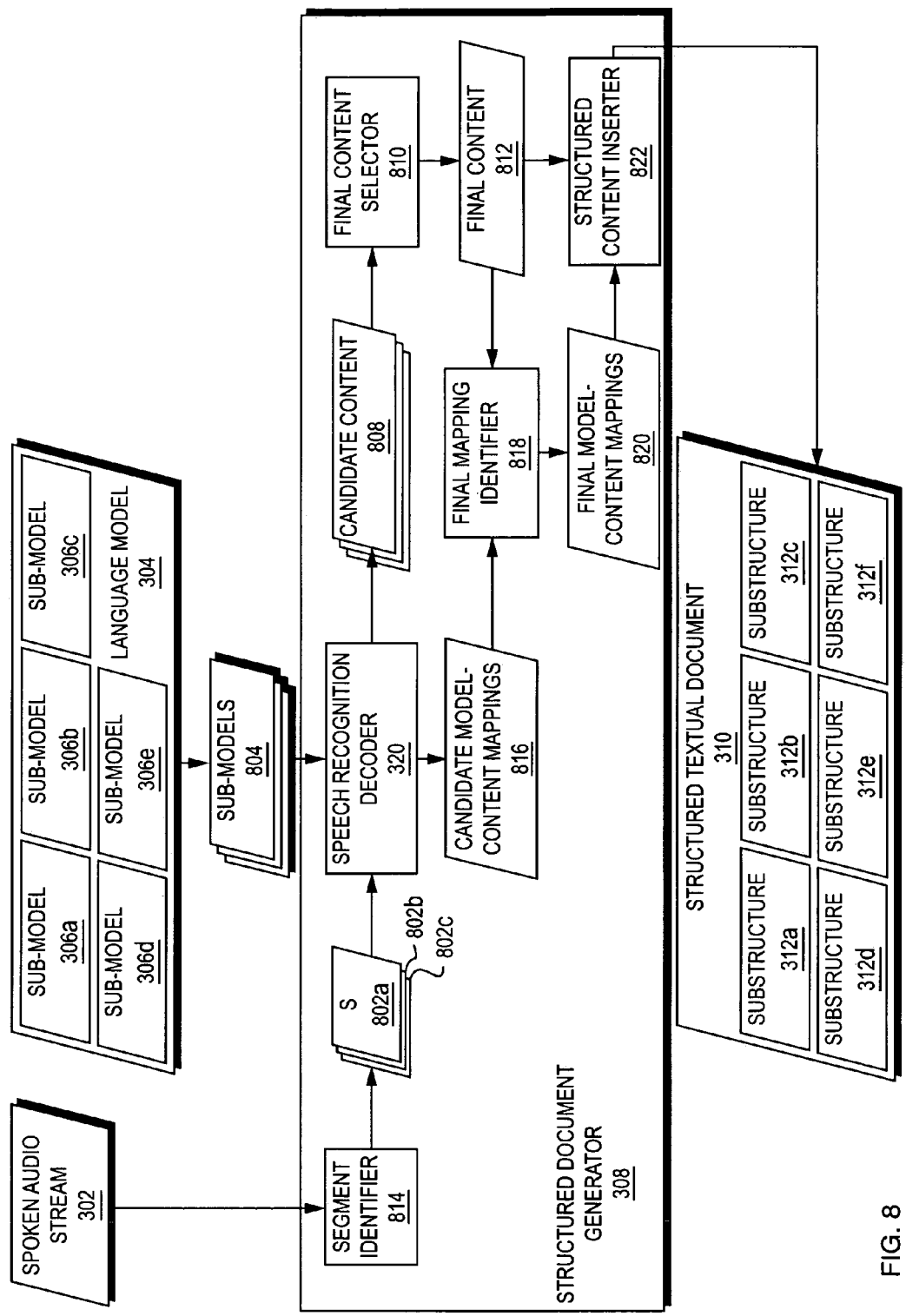
FIG. 8 is a dataflow diagram illustrating a portion of the system of FIG. 3 in detail relevant to the method of FIG. 7 according to one embodiment of the present invention.

Having generally described features of various embodiments of the present invention, embodiments of the present invention will now be described in more detail. Referring to FIG. 7, a flowchart is shown of a method that is performed by the structured document generator 308 in one embodiment of the present invention to generate the structured textual document 310 (FIG. 2, step 204). Referring to FIG. 8, a dataflow diagram is shown illustrating a portion of the system 300 in detail relevant to the method of FIG. 7.

In the example illustrated in FIG. 8, the structured document generator 308 includes a segment identifier 814 which identifies a plurality of segments S 802a-c in the spoken audio stream 302 (step 701). The segments 802a-c may, for example, represent concepts such as sections, paragraphs, sentences, words, dates, times, or codes. Although only three segments 802a-c are shown in FIG. 8, the spoken audio stream 302 may include any number of portions. Although for ease of explanation, all of the segments 802a-c are identified in step 701 of FIG. 7 prior to performing the remainder of the method 700, the identification of the segments 802a-c may be performed concurrently with recognizing the audio stream 302 and generating the structured document 310, as will be described in more detail below with respect to FIGS. 11B and 12B.

The structured document generator 308 enters a loop over each segment S in the spoken audio stream 302 (step 702). As described above, the structured document generator 308 includes speech recognition decoder 320, which may, for example, include one or more conventional speech recognition decoders for recognizing speech using different kinds of language models. As further described above, each of the sub-models 306a-e may be an n-gram language model, a context-free grammar, or a combination of both.

Assume for purposes of example that the structured document generator 308 is currently processing segment 802a of the spoken audio stream 302. The structured document generator 308 selects a plurality 804 of the sub-models 306a-e with which to recognize the current segment S. The sub-models 804 may, for example, be all of the language sub-models 306a-e or a subset of the sub-models 306a-e. The speech recognition decoder 320 recognizes the current segment S (e.g., segment 802a) with each of the selected sub-models 804, thereby producing a plurality of candidate contents 808 corresponding to segment S (step 704). In other words, each of the candidate contents 808 is produced by using the speech recognition decoder 320 to recognize the current segment S using a distinct one of the sub-models 804. Note that each of the candidate contents 808 may include not only recognized text but also other kinds of content, such as concepts (e.g., dates, times, codes, medications, allergies, vitals, etc.) encoded in machine-readable form.

The structured document generator 308 includes a final content selector 810 which selects one of the candidate contents 808 as a final content 812 for segment S (step 706). The final content selector 810 may use any of a variety of techniques that are well-known to those of ordinary skill in the art for selecting speech recognition output that most closely matches speech from which the output was derived.

Figure 9:
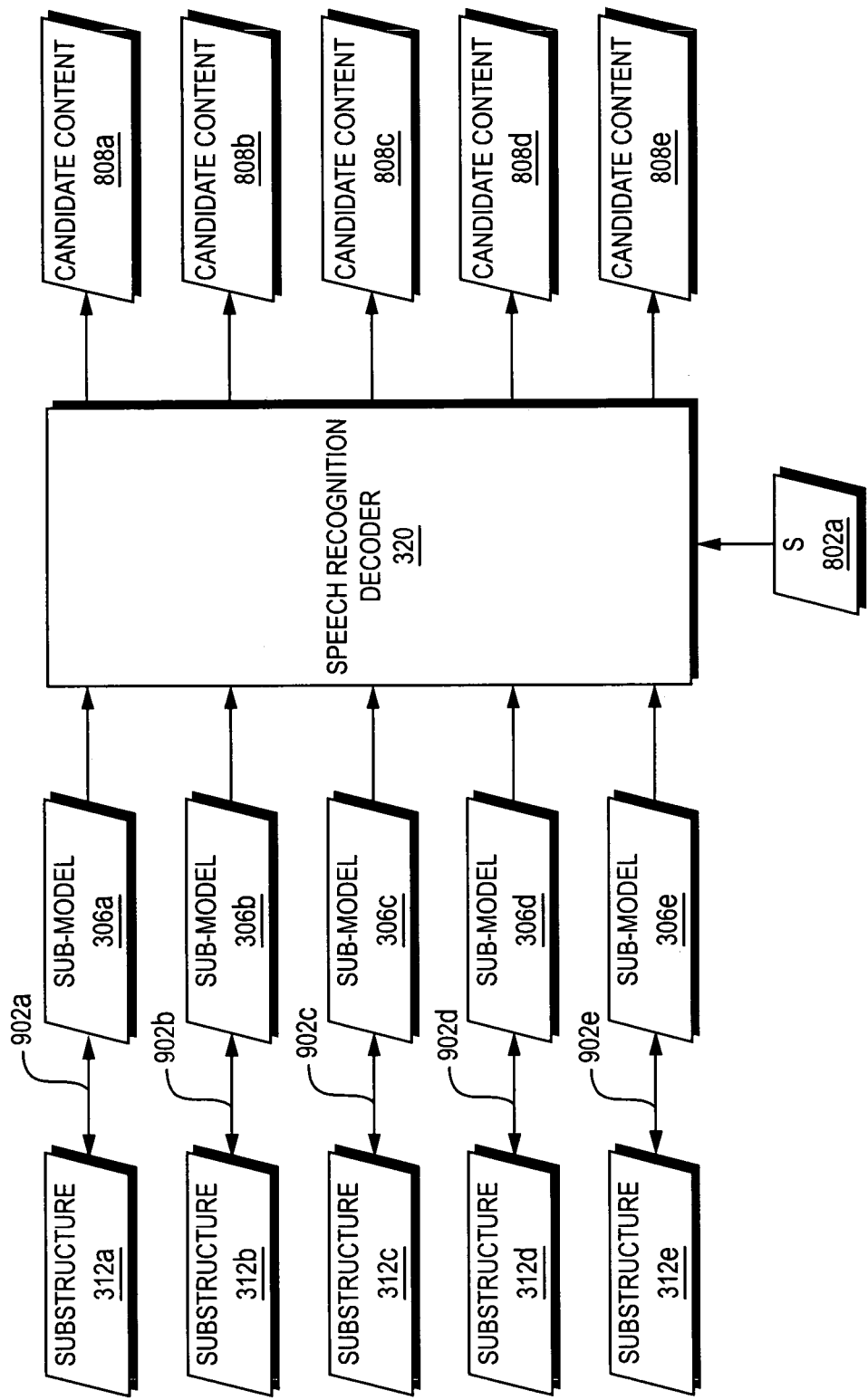
FIG. 9 is a diagram illustrating mappings between language models, document sub-structures corresponding to the language models, and candidate contents produced using the language models according to one embodiment of the present invention.

The structured document generator 308 keeps track of the sub-model that is used to produce each of the candidate contents 808. Assume, for purposes of example, that the sub-models 304 include all of the sub-models 306a-e, and that the candidate contents 808 therefore include five candidate contents per segment 802a-c (one produced using each of the sub-models 306a-e). For example, referring to FIG. 9, a diagram is shown illustrating mappings between the document sub-structures 312a-f, the sub-models 306a-e, and candidate contents 808a-e. As described above, each of the sub-models 306a-e may be associated with one or more corresponding sub-structures 312a-f in the structured textual document 310. These correspondences are indicated in FIG. 9 by mappings 902a-e between the sub-structures 312a-e and the sub-models 306a-e. The structured document generator 308 may maintain such mappings 902a-e in a table or using other means.

When the speech recognition decoder 320 recognizes segment S (e.g., segment 802a) with each of the sub-models 306a-e, it produces corresponding candidate contents 808a-e. For example, candidate content 808a is the text that is produced when speech recognition decoder 320 recognizes segment 802a with sub-model 306a, candidate content 808b is the text that is produced when speech recognition decoder 320 recognizes segment 802a with sub-model 306b, and so on. The structured document generator 308 may record the mapping between candidate contents 808a-e and corresponding sub-models 306a-e in a set of candidate model-content mappings 816.

Therefore, when the structured document generator 308 selects one of the candidate contents 808a-e as the final content 812 for segment S (step 706), a final mapping identifier 818 may use the mappings 816 and the selected final content 812 to identify the language sub-model that produced the candidate content that has been selected as the final content 812 (step 708). For example, if candidate content 808c is selected as the final content 812, it may be seen from FIG. 9 that the final mapping identifier 818 may identify the sub-model 306c as the sub-model that produced candidate content 808c. The final mapping identifier 818 may accumulate each identified sub-model in the set of mappings 820, so that at any given time the mappings 820 identify the sequence of language sub-models that were used to generate the final contents that have been selected for inclusion in the structured textual document 310.

Once the sub-model corresponding to the final content 812 has been identified, the structured document generator 308 may identify the document sub-structure associated with the identified sub-model (step 710). For example, if the sub-model 306c has been identified in step 708, it may be seen from FIG. 9 that document sub-structure 312c is associated with sub-model 306c.

A structured content inserter 822 inserts the final content 812 into the identified sub-structure of the structured text document 310 (step 712). For example, if the sub-structure 312c is identified in step 710, the text inserter 514 inserts the final content 812 into sub-structure 312c.

The structured document generator repeats steps 704-712 for the remaining segments 802b-c of the spoken audio stream 302 (step 714), thereby generating final content 812 for each of the remaining segments 802b-c and inserting the final content 812 into the appropriate ones of the sub-structures 312a-f of the textual document 310. Upon conclusion of the method 700, the structured textual document 310 includes text corresponding to the spoken audio stream 302, and the final model-content mappings 820 identify the sequence of language sub-models that were used by the speech recognition decoder 320 to generate the text in the structured textual document 310.

Note that in the process of recognizing the spoken audio stream 302, the method 700 may not only generate text corresponding to the spoken audio, but may also identify semantic information represented by the audio and store such semantic information in a machine-readable form. For example, referring again to FIG. 5, the comparison section 312b includes a date element in which a particular date is represented as a triplet containing individual values for the day ("06"), month ("APR"), and year ("2001"). Other examples for semantic concepts in the medical domain include vital signs, medications and their dosages, allergies, medical codes, etc. Extracting and representing semantic information in this way facilitates the process of performing automated processing on such information. Note that the particular form in which semantic information is represented in FIG. 5 is merely an example and does not constitute a limitation of the present invention.

Recall from step 701 that the method 700 shown in FIG. 7A identifies the set of segments 802a-c before identifying the sub-models to be used to recognize the segments 802a-c. Note, however, that the structured document generator 308 may integrate the process of identifying the segments 802a-c with the process of identifying the sub-models to be used to recognize the segments 802a-c, and with the process of performing speech recognition on the segments 802a-c. Examples of techniques that may be used to perform such integrated segmentation and recognition will be described in more detail below with respect to FIGS. 11B and 12B.

Having generally described the operation of the method illustrated in FIG. 7, consider now the application of the method of FIG. 7 to the example audio stream 302 shown in FIG. 4. Assume that the first portion of the spoken audio stream 302 is the spoken stream of utterances: "CT scan of the chest without contrast april twenty second two thousand three". This portion may be selected in step 702 and recognized using all of the language sub-models 306a-e in step 704 to produce a plurality of candidate contents 808a-e. As described above, assume that sub-model 306a is a "header" language model, that sub-model 306b is a "comparison" language model, that sub-model 306c is a "technique" language model, that sub-model 306d is a "findings" language model, and that sub-model 306e is an "impression" language model.

Because sub-model 306a is a language model which has been trained to recognize speech in the "header" section of the document 310 (e.g., sub-structure 312a), it is likely that the candidate content 808a produced using sub-model 306a will match the words in the above-referenced audio portion more closely than the other candidate contents 808b-e. Assuming that the candidate content 808a is selected as the final content 812 for this audio portion, the content inserter 822 will insert the final content 812 produced by sub-model 306a into the header section 312a of the structured text document 310.

Assume that the second portion of the spoken audio stream is the spoken stream of utterances: "comparison to prior studies from march twenty six two thousand two and april six two thousand one". This portion may be selected in step 702 and recognized using all of the language sub-models 306a-e in step 704 to produce a plurality of candidate contents 808a-e. Because sub-model 306b is a language model which has been trained to recognize speech in the "comparison" section of the document 310 (e.g., sub-structure 312b), it is likely that the candidate content 808b produced using sub-model 306b will match the words in the above-referenced audio portion more closely than the other candidate contents 808a and 808c-e. Assuming that the candidate content 808b is selected as the final content 812 for this audio portion, the text inserter 514 will insert the final content 812 produced by sub-model 306b into the comparison section 312b of the structured text document 310.

The remainder of the audio stream 302 illustrated in FIG. 4 may be recognized and inserted into appropriate ones of the sub-structures 312a-f in the structured textual document 310 in a similar manner. Note that although content in the spoken audio stream 302 illustrated in FIG. 4 appears in the same sequence as the sections 312a-f in the structured textual document 310, this is not a requirement of the present invention. Rather, content may appear in the audio stream 302 in any order. Each of the segments 802a-c of the audio stream 302 is recognized by the speech recognition decoder 320, and the resulting final content 812 is inserted into the appropriate one of the sub-structures 312a-f. As a result, the order of the textual content in the sub-structures 312a-f may not be the same as the order of the content in the spoken audio stream. Note, however, that even if the order of textual content is the same in both the audio stream 302 and the structured textual document 310, the rendering engine 314 (FIG. 3) may render the textual content of the document 310 in any desired order.

In another embodiment of the present invention, the probabilistic language model 304 is a hierarchical language model. In particular, in this embodiment the plurality of sub-models 306a-e are organized in a hierarchy. As described above, the sub-models 306a-e may further include additional sub-models, and so on, so that the hierarchy of the language model 304 may include multiple levels.

Figure 10A:
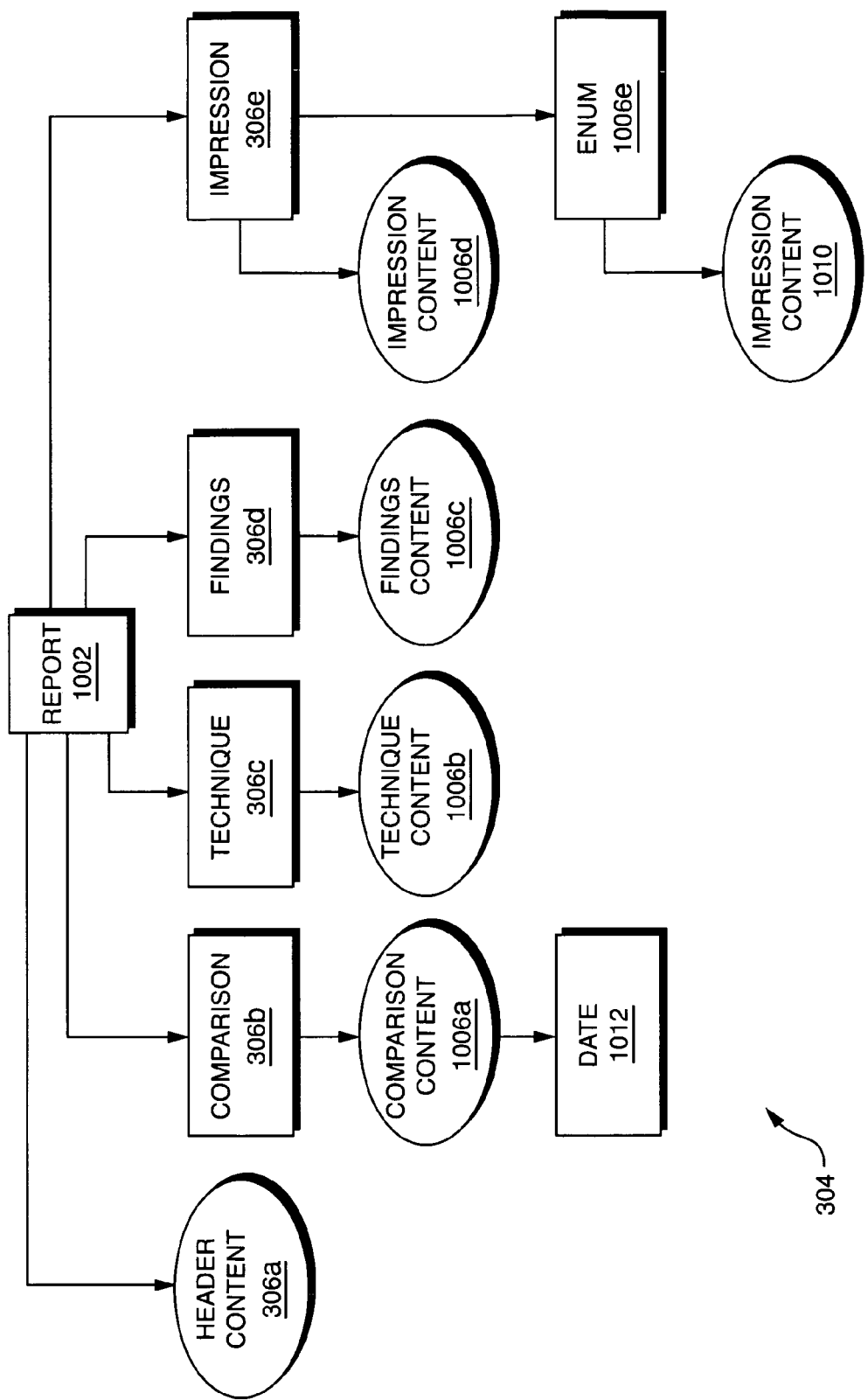
FIG. 10A is a diagram illustrating a hierarchical language model according to one embodiment of the present invention.

Referring to FIG. 10A, a diagram is shown illustrating an example of the language model 304 in hierarchical form. The language model 304 includes a plurality of nodes 1002, 306a-e, 1006a-e, and 1010 and 1012. Square nodes 1002, 306b-e, and 1006e and 1012 use probabilistic finite state grammars to model highly constrained concepts (such as report section order, section cues, dates, and times). Elliptical nodes 306a, 1006a-d, and 1010 use statistical (n-gram) language models to model less-constrained language.

The term "concept" as used herein includes, for example, dates, times, numbers, codes, medications, medical history, diagnoses, prescriptions, phrases, enumerations and section cues. A concept may be spoken in a plurality of ways. Each way of speaking a particular concept is referred to herein as a "spoken form" of the concept. A distinction is sometimes made between "semantic" concepts and "syntactic" concepts. The term "concept" as used herein includes both semantic concepts and syntactic concepts, but is not limited to either and does not rely on any particular definition of "semantic concept" or "syntactic concept" or on any distinction between the two.

Consider, for example, the date Oct. 1, 1993, which is an example of a concept as that term is used herein. Spoken forms of this concept include the spoken phrases, "october first nineteen ninety three," "one october ninety three," and "ten dash one dash ninety three." Text such as "Oct. 1, 1993" and "10/01/1993" are examples of "written forms" of this concept.

Now consider the sentence "John Jones has pneumonia." This sentence, which is a concept as that term is used herein, may be spoken in a plurality of ways, such as the spoken phrases, "john jones has pneumonia," "patient jones diagnosis pneumonia," and "diagnosis pneumonia patient jones." The written sentence "John Jones has pneumonia" is an example of a "written form" of the same concept.

Although language models for low-level concepts such as dates and times are not shown in FIG. 10A (except for sub-model 1012), the hierarchical language model 304 may include sub-models for such low-level concepts. For example, the n-gram sub-models 306a, 1006a-d, and 1010 may assign probabilities to sequences of words representing dates, times, and other low-level concepts.

The language model 304 includes root node 1002, which contains a finite state grammar representing the probabilities of occurrence of node 1002's sub-nodes 306a-e. The root node 1002 may, for example, indicate probabilities of the header, comparison, technique, findings, and impression sections of the document 310 appearing in particular orders in the spoken audio stream 302.

Moving down one level in the hierarchy of language model 304, node 306a is a "header" node, which is an n-gram language model representing probabilities of occurrence of words in portions of the spoken audio stream 302 intended for inclusion in the header section 312a of the structured textual document 310.

Node 306b contains a "comparison" finite state grammar representing probabilities of occurrence of a variety of alternative spoken forms of cues for the comparison section 312b of the textual document. The finite state grammar in the comparison node 306b may, for example, include cues such as "comparison to", "comparison for", "prior is", and "prior studies are". The finite state grammar may include a probability for each of these cues. Such probabilities may, for example, be based on observed frequencies of use of the cues in a set of training speech for the same speaker or in the same domain as the spoken audio stream 302. Such frequencies may be obtained, for example, using the techniques disclosed in the above-reference patent application entitled "Document Transcription System Training."

The comparison node 306b includes a "comparison content" sub-node 1006a, which is an n-gram language model representing probabilities of occurrence of words in portions of the spoken audio stream 302 intended for inclusion in the body of the comparison section 312b of the textual document 310. The comparison content node 1006a has a date node 1012 as a child. As will be described in more detail below, the date node 1012 is a finite state grammar representing probabilities of the date being spoken in various ways.

Nodes 306c and 306d may be understood similarly. Node 306c contains a "technique" finite state grammar representing probabilities of occurrence of a variety of alternative spoken forms of cues for the technique section 312c of the textual document 310. The technique node 306c includes a "technique content" sub-node 1006b, which is an n-gram language model representing probabilities of occurrence of words in portions of the spoken audio stream 302 intended for inclusion in the body of the technique section 312c of the textual document 310. Similarly, node 306d contains a "findings" finite state grammar representing probabilities of occurrence of a variety of alternative spoken forms of cues for the findings section 312d of the textual document 310. The findings node 306d includes a "findings content" sub-node 1006c, which is an n-gram language model representing probabilities of occurrence of words in portions of the spoken audio stream 302 intended for inclusion in the body of the findings section 312d of the textual document 310.

Impression node 306e is similar to nodes 306b-d, in that it includes a finite state grammar for recognizing section cues and a sub-node 1006d including an n-gram language model for recognizing section content. In addition, however, the impression node 306e includes an additional sub-node 1006e, which in turn includes a sub-node 1010. This indicates that the content of the impression section may be recognized using either the language model in the impression content node 1006d or the "enum" node 1006e, governed by the finite state grammar-based language model corresponding to impression node 306e. The "enum" node 1006e contains a finite state grammar indicating probabilities associated with different ways of speaking enumeration cues (such as "number one," "number two," "first," "second," "third," and so on). The impression content node 1010 may include the same language model as the impression content node 1006d.

Figure 11A:
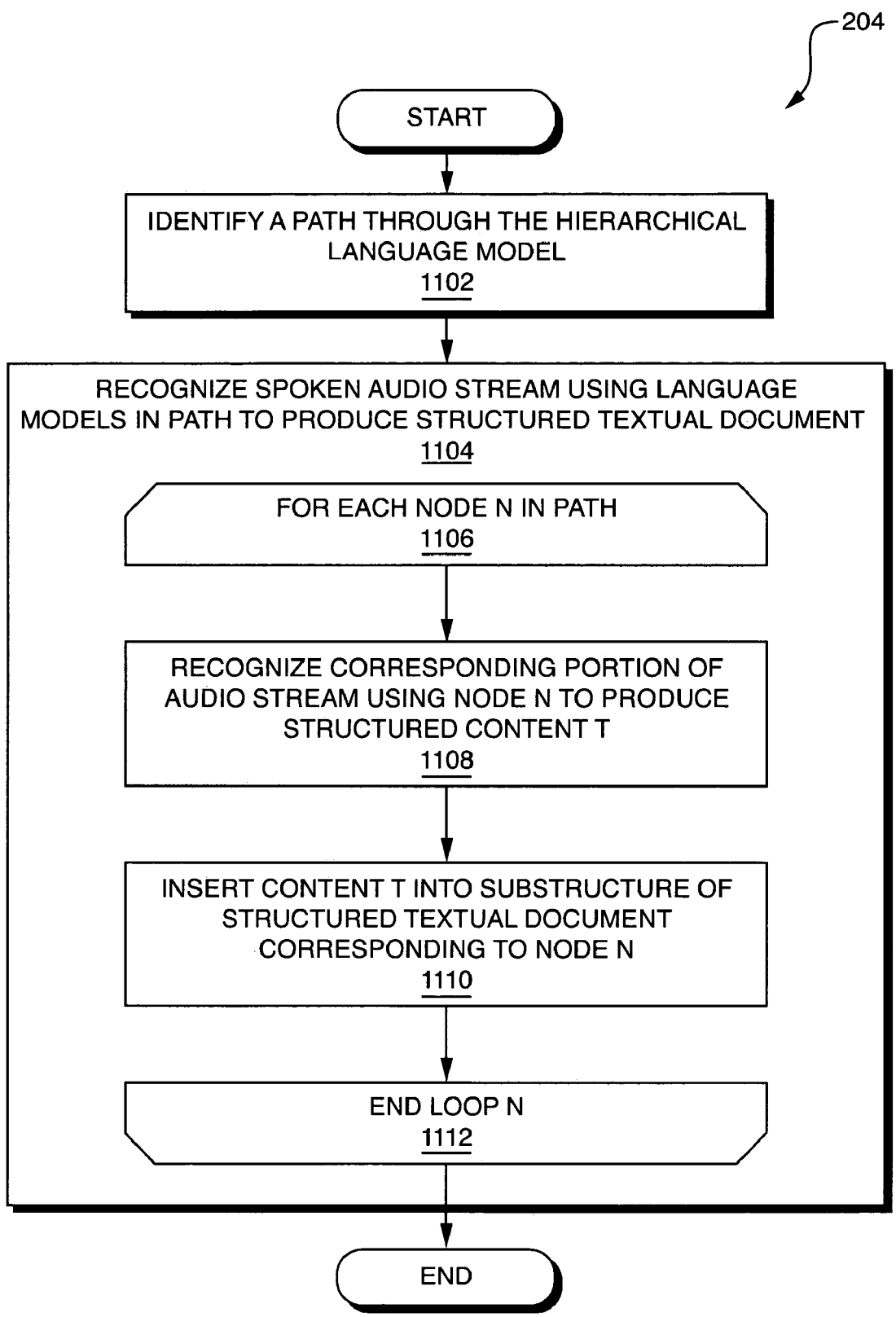
FIG. 11A is a flowchart of a method that is performed by the structured document generator of FIG. 3 to generate a structured textual document according to one embodiment of the present invention.
Figure 12A:
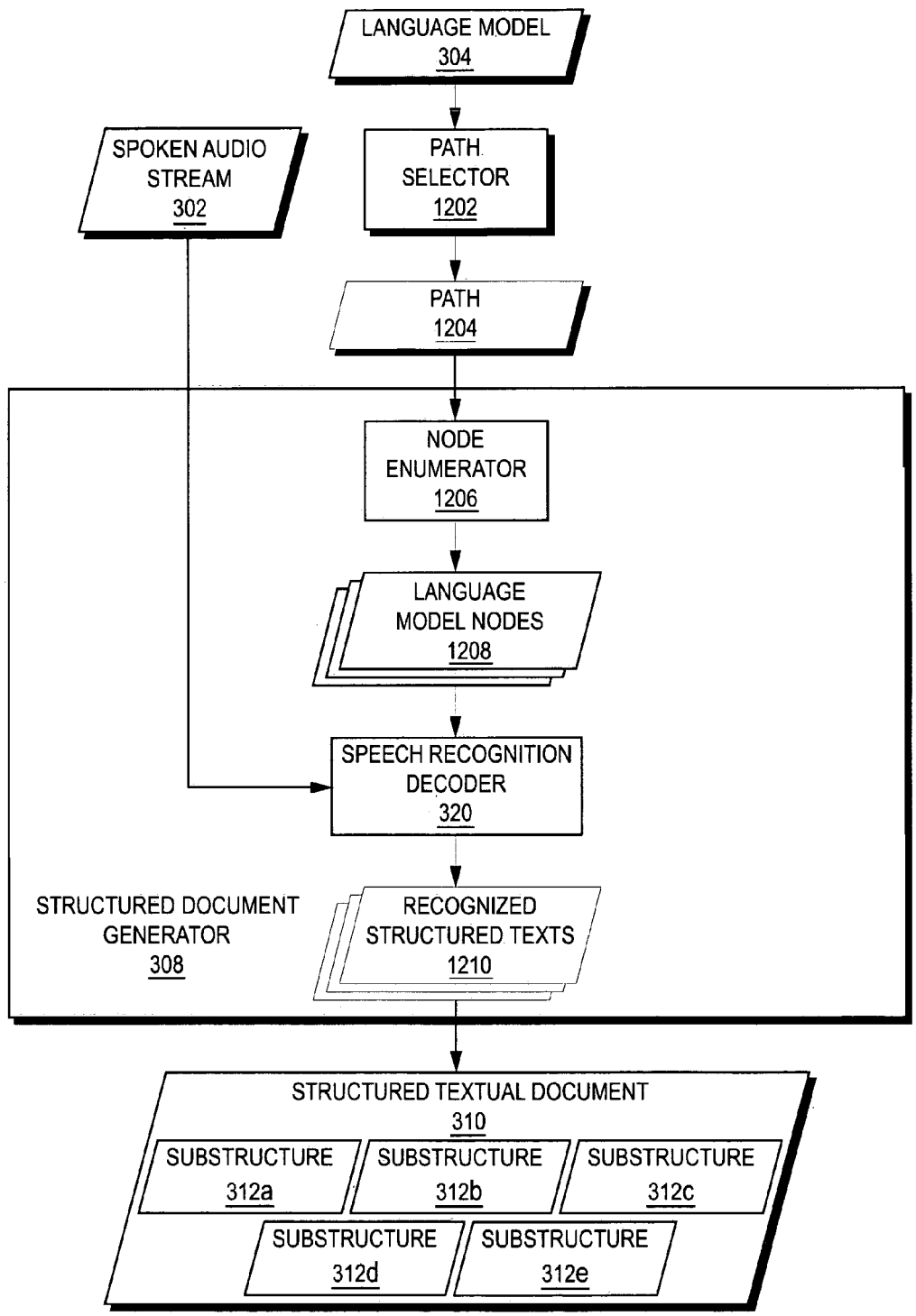
FIG. 12A is a dataflow diagram illustrating a portion of the system of FIG. 3 in detail relevant to the method of FIG. 11A according to one embodiment of the present invention.

Having described the hierarchical structure of the language model 304 in one embodiment of the present invention, examples of techniques that may be used to generate the structured document 310 using the language model 304 will now be described. Referring to FIG. 11A, a flowchart is shown of a method that is performed by the structured document generator 308 in one embodiment of the present invention to generate the structured textual document 310 (FIG. 2, step 204). Referring to FIG. 12A, a dataflow diagram is shown illustrating a portion of the system 300 in detail relevant to the method of FIG. 11A.

The structured document generator 308 includes a path selector 1202 which identifies a path 1204 through the hierarchical language model 304 (step 1102). The path 1204 is an ordered sequence of nodes in the hierarchical language model 304. Nodes may be traversed multiple times in the path 1204. Examples of techniques for generating the path 1204 will be described in more detail below with respect to FIGS. 11B and 12B.

Figure 10B:
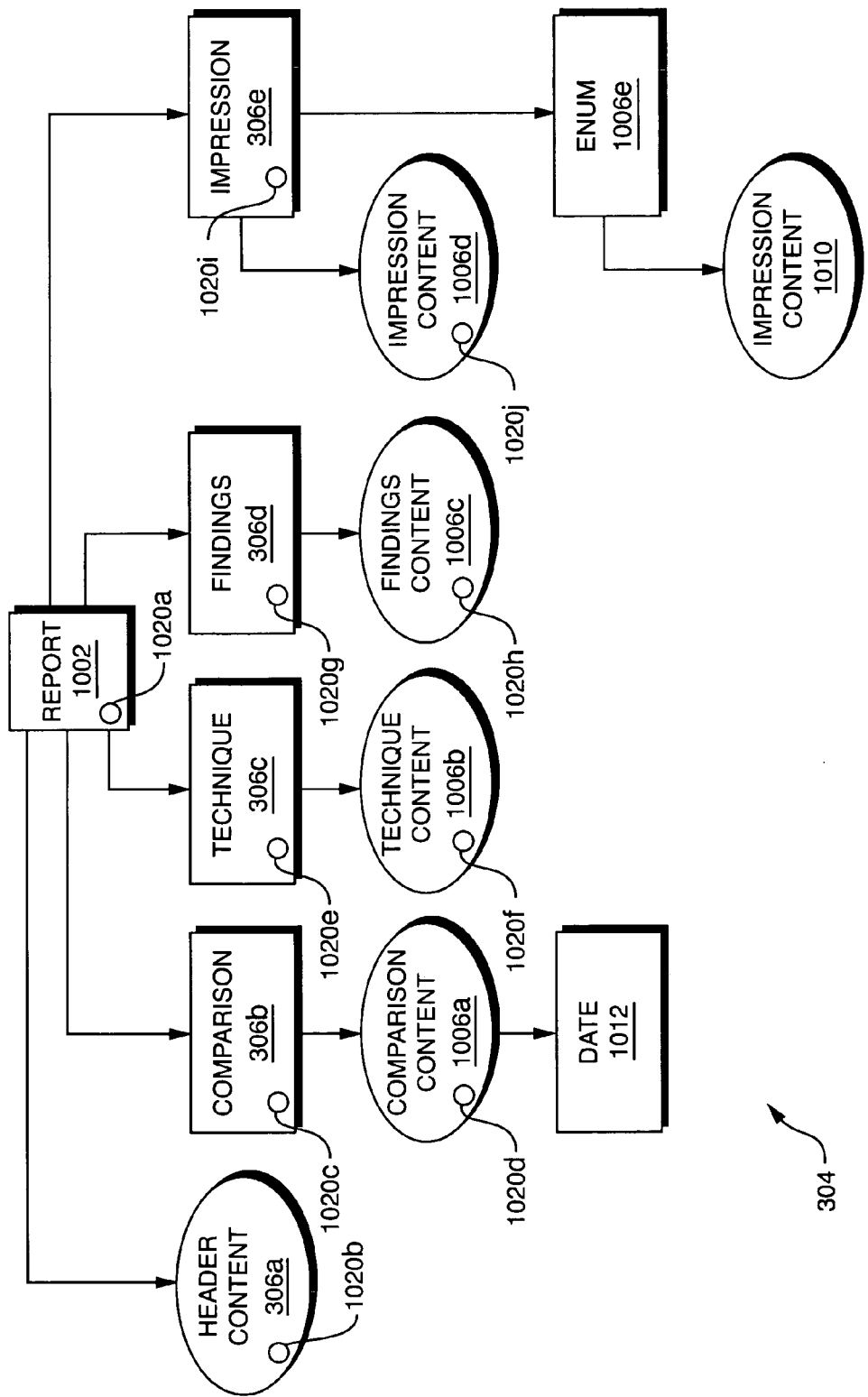
FIG. 10B is a diagram illustrating a path through the hierarchical language model of FIG. 10A according to one embodiment of the present invention.

Referring to FIG. 10B, an example of the path 1204 is illustrated. The path 1204 includes points 1020a-j, which specify a sequence in which to traverse nodes in the language model 304. Points 1020a-j are referred to as "points" rather than "nodes" to distinguish them from nodes 1002, 306a-e, 1006a-e, and 1010 in the language model 304.

In the example illustrated in FIG. 10B, path 1204 traverses the following nodes of language model 304 in sequence: (1) root node 1002 (point 1020a); (2) header content node 306a (point 1020b); (3) comparison node 306b (point 1020c); (4) comparison content node 1006a (point 1020d); (5) technique node 306c (point 1020e); (6) technique content node 1006b (point 1020f); (7) findings node 306d (point 1020g); (8) findings content node 1006c (point 1020h); (9) impression node 306e (point 1020i); and (10) impression content node 1006d (point 1020j).

As may be seen by reference to FIG. 4, recognizing the spoken audio stream 302 using the language sub-models falling along the path 1204 illustrated in FIG. 10B would result in optimal speech recognition, since speech in the audio stream 302 occurs in the same sequence as the language sub-models in the path 1204 illustrated in FIG. 10B. For example, the spoken audio stream 302 begins with speech that is best recognized by the header content language model 306a ("CT scan of the chest without contrast april twenty second two thousand three"), followed by speech that is best recognized by the comparison language model 306b ("comparison to"), followed by speech that is best recognized by the comparison content language model 1006a ("prior studies from march twenty six two thousand two and april six two thousand one"), and so on.

Having identified the path 1204, the structured document generator 308 recognizes the spoken audio stream 302 using the language models traversed by the path 1204 to produce the structured textual document 310 (step 1104). As described in more detail below with respect to FIGS. 11B and 12B, the speech recognition and structured textual document generation of step 1104 may be integrated with the path identification of step 1102, rather than performed separately.

More specifically, the structured document generator 308 may include a node enumerator 1206 which iterates over each of the language model nodes N 1208 traversed by the selected path 1204 (step 1106). For each such node N, the speech recognition decoder 320 may recognize the portion of the audio stream 302 corresponding to the language model at node N to produce corresponding structured text T (step 1108). The structured document generator 308 may insert text T 1210 into the substructure of the structured textual document 310 corresponding to node N 1208 of the language model 304 (step 1110).

For example, when node N is the comparison node 306b (FIG. 10A), the comparison node 306b may be used to recognize the text "comparison to" in the spoken audio stream 302 (FIG. 4). Because comparison node 306b corresponds to a document sub-structure (e.g., the comparison section 312b)

rather than to content, the result of the speech recognition performed in step 1108 in this case may be a document substructure, namely an empty "comparison" section. Such a section may be inserted into the structured document 310 in step 1110, for example, in the form of matching "<comparison>" and "</comparison>" tags.

When node N is the comparison content node 1006a (FIG. 10A), the comparison content node 1006a may be used to recognize the text "prior studies from march twenty six two thousand two and april six two thousand one" in the spoken audio stream 302 (FIG. 4), thereby producing the structured text "Prior studies from <date>26-MAR-2002</date> and <date>06-APR-2001</date>", as shown in FIG. 5. This structured text may then be inserted into the comparison section 312b in step 1110 (e.g., between the "<comparison>" and "</comparison>" tags, as shown in FIG. 5).

The structured document generator 308 repeats steps 1108-1110 for the remaining nodes N traversed by the path 1204 (step 1112), thereby inserting a plurality of structured texts 1210 into the structured textual document 310. The end result of the method illustrated in FIG. 11A is the creation of the structured textual document 310, which contains text having a structure that corresponds to the structure of the path 1204 through the language model 304. For example, it can be seen from FIG. 10B that the structure of the illustrated path traverses language model nodes corresponding to the header, comparison, technique, findings, and impression sections in sequence. The resulting structured textual document 310 (as illustrated, for example, in FIG. 5) similarly includes header, comparison, technique, findings, and impression sections in sequence. The structured textual document 310 therefore has the same structure as the language model path 1204 that was used to create the structured textual document 310.

It was stated above that the structured document generator 308 inserts recognized structured text 1210 into the appropriate sub-structures of the structured textual document 310 (FIG. 11A, step 1110). As shown in FIG. 5, the structured textual document 310 may be implemented as an XML document or other document which supports nested structures. In such a case, it is necessary to insert each of the recognized structured texts 1210 inside of the appropriate substructure so that the final structured textual document 310 has a structure that corresponds to the structure of the path 1204. Those having ordinary skill in the art will understand how to use the final model-content mappings 820 (FIG. 8) to use the path 1204 to traverse the structure of the language model 304 and thereby to create such a structured document.

The system illustrated in FIG. 12A includes path selector 1202, which selects a path 1204 through the language model 304. The method illustrated in FIG. 11A then uses the selected path 1204 to generate the structured textual document 310. In other words, in FIGS. 11A and 12A, the steps of path selection and structured document creation are performed separately. This is not, however, a limitation of the present invention.

Figure 11B:
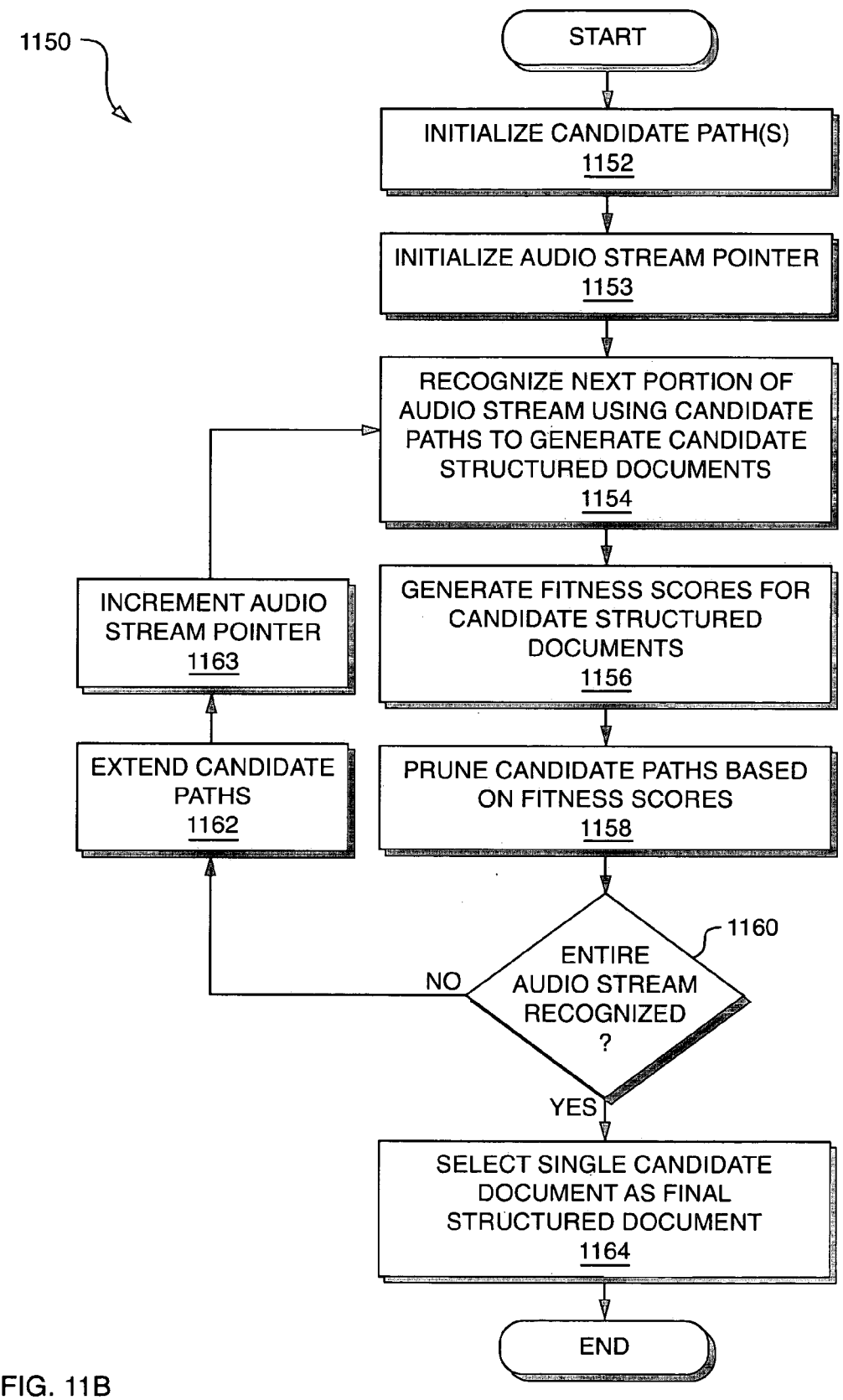
FIG. 11B is a flowchart of a method which uses an integrated process to select a path through a hierarchical language model and to generate a structured textual document based on speech according to one embodiment of the present invention.
Figure 12B:
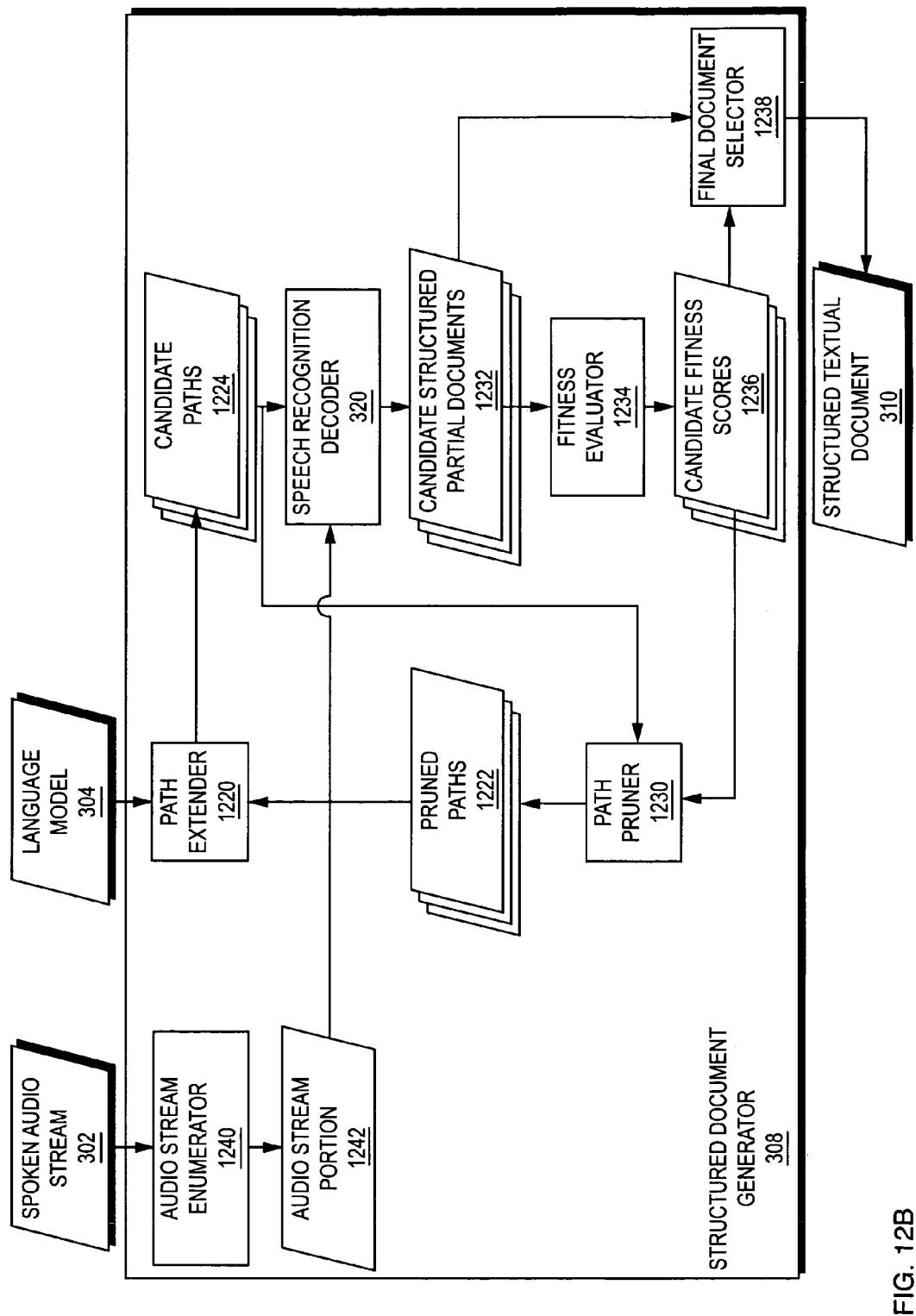
FIG. 12B is a dataflow diagram illustrating an embodiment of the structured document generator of FIG. 3 which performs the method of FIG. 11B in one embodiment of the present invention.

Rather, referring to FIG. 11B, a flowchart is shown of a method 1150 which integrates the steps of path selection and structured document generation. Referring to FIG. 12B, an embodiment of the structured document generator 308 is shown which performs the method 1150 of FIG. 11B in one embodiment of the present invention. In overview, the method 1150 of FIG. 11B searches for possible paths through the hierarchy of the language model 304 (FIG. 10A), beginning at the root node 1002 and expanding outward. Any of a variety of techniques, including techniques well-known to those of ordinary skill in the art, may be used to search through the language model hierarchy. As the method 1150 identifies partial paths through the language model hierarchy, the method 1150 uses the speech recognition decoder 320 to recognize increasingly large portions of the spoken audio stream 302 using the language models falling along the partial paths, thereby creating partial candidate structured documents. The method 1150 assigns fitness scores to each of the partial candidate structured documents. The fitness score for each candidate structured document is a measure of how well the path that produced the candidate structured document has performed. The method 1150 expands the partial paths, thereby continuing to search through the language model hierarchy, until the entire spoken audio stream 302 has been recognized. The structured document generator 308 selects the candidate structured document having the highest fitness score as the final structured textual document 310.

More specifically, the method 1150 initializes one or more candidate paths 1224 through the language model 304 (step 1152). For example, the candidate paths 1224 may be initialized to contain a single path consisting of the root node 1002. The term "frame" refers herein to a short period of time, such as 10 milliseconds. The method 1150 initializes an audio stream pointer to point to the first frame in the audio stream 302 (step 1153). For example, in the embodiment illustrated in FIG. 12B, the structured document generator 308 contains an audio stream enumerator 1240 which provides a portion 1242 of the audio stream 302 to the speech recognition decoder 320. Upon initiation of the method 1150, the portion 1242 may solely contain the first frame of the audio stream 302.

The speech recognition decoder 320 recognizes the current portion 1242 of the audio stream 302 using the language sub-models in the candidate path(s) 1224 to generate one or more candidate structured partial documents 1232 (step 1154). Note that the documents 1232 are only partial documents 1232 because they have been generated based on only a portion of the audio stream 302. When step 1154 is first performed, the speech recognition decoder 320 may simply recognize the first frame of the audio stream 302 using the language model at the root node 1002 of the language model 304.

Note that the techniques disclosed above with respect to FIG. 11A and FIG. 12A may be used by the speech recognition decoder 320 to generate the candidate structured partial documents 1232 using the candidate paths 1224. More specifically, the speech recognition decoder 320 may apply the methods illustrated in FIG. 11A to the audio stream portion 1242 using each of the candidate paths 1224 as the path identified in step 1102 (FIG. 11A).

Returning to FIGS. 11B and 12B, a fitness evaluator 1234 generates fitness scores 1236 for each of the candidate structured partial documents 1232 (step 1156). The fitness scores 1236 are measures of how well the candidate structured partial documents 1232 represent the corresponding portion of the audio stream 302. In general, the fitness score for a single candidate document may be generated by: (1) generating fitness scores for each of the nodes in the corresponding one of the candidate paths 1224; and (2) using a synthesis function to synthesize the individual node fitness scores generated in step (1) into an overall fitness score for the candidate structured document. Examples of techniques that may be used to generate the candidate fitness scores 1236 will be described in more detail below with respect to FIG. 11C.

If the structured document generator 308 were to attempt to search for all possible paths through the hierarchy of the language model 304, the computational resources required to evaluate each possible path might become prohibitively costly and/or time-consuming due to the exponential growth in the number of possible paths. Therefore, in the embodiment illustrated in FIG. 12B, a path pruner 1230 uses the candidate fitness scores 1236 to remove poorly-fitting paths from the candidate paths 1224, thereby producing a set of pruned paths 1222 (step 1158).

If the entire audio stream 302 has been recognized (step 1160), a final document selector 1238 selects, from among the candidate structured partial documents 1232, the candidate structured document having the highest fitness score, and provides the selected document as the final structured textual document 310 (step 1164). If the entire audio stream 302 has not been recognized, a path extender 1220 extends the pruned paths 1222 within the language model 304 to produce a new set of candidate paths 1224 (step 1162). If, for example, the pruned paths 1222 consist of a single path containing the root node 1002, the path extender 1220 may extend this path by one node downward in the hierarchy illustrated in FIG. 10A to produce a plurality of candidate paths extending from the root node 1002, such as a path from the root node 1002 to the header content node 306*a*, a path from the root node 1002 to the comparison node 306*b*, a path from the root node 1002 to the technique node 306*c*, and so on. Various techniques for extending the paths 1224 to perform depth-first, breadth-first, or other kinds of hierarchical searches are well-known to those having ordinary skill in the art.

The audio stream enumerator 1240 extends the portion 1242 of the audio stream 302 to include the next frame in the audio stream 302 (step 1163). Steps 1154-1160 are then repeated by using the new candidate paths 1224 to recognize the portion 1242 of the audio stream 302. In this way the entire audio stream 302 may be recognized using appropriate sub-models in the language model 304.

As described above with respect to FIGS. 11B and 12B, fitness scores 1236 may be generated for each of the candidate structured partial documents 1232 produced by the structured document generator 308 while evaluating candidate paths 1224 through the language model 304. Examples of techniques will now be described for generating fitness scores, either for the partial candidate structured partial documents 1232 illustrated in FIG. 12B or for structured documents more generally.

For example, referring to FIG. 10A, note that the comparison content node 1006*a* has a date node 1012 as a child. Assume that the text "CT scan of the chest without contrast april twenty second two thousand three" has been recognized as text corresponding to the comparison content node 1006*a*. Note that the comparison content node 1006*a* was used to recognize the text "CT scan of the chest without contrast" and that the date node 1012, which is a child of the comparison content node 1006*a*, was used to generate the text "april twenty second two thousand three". The fitness score for this text may, therefore, be calculated by using the comparison content node 1006*a* to calculate a first fitness score for the text "CT scan of the chest without contrast" followed by any date, calculating a second fitness score for the text "april twenty second two thousand three" based on the date node 1012, and multiplying the first and second fitness scores.

Figure 11C:
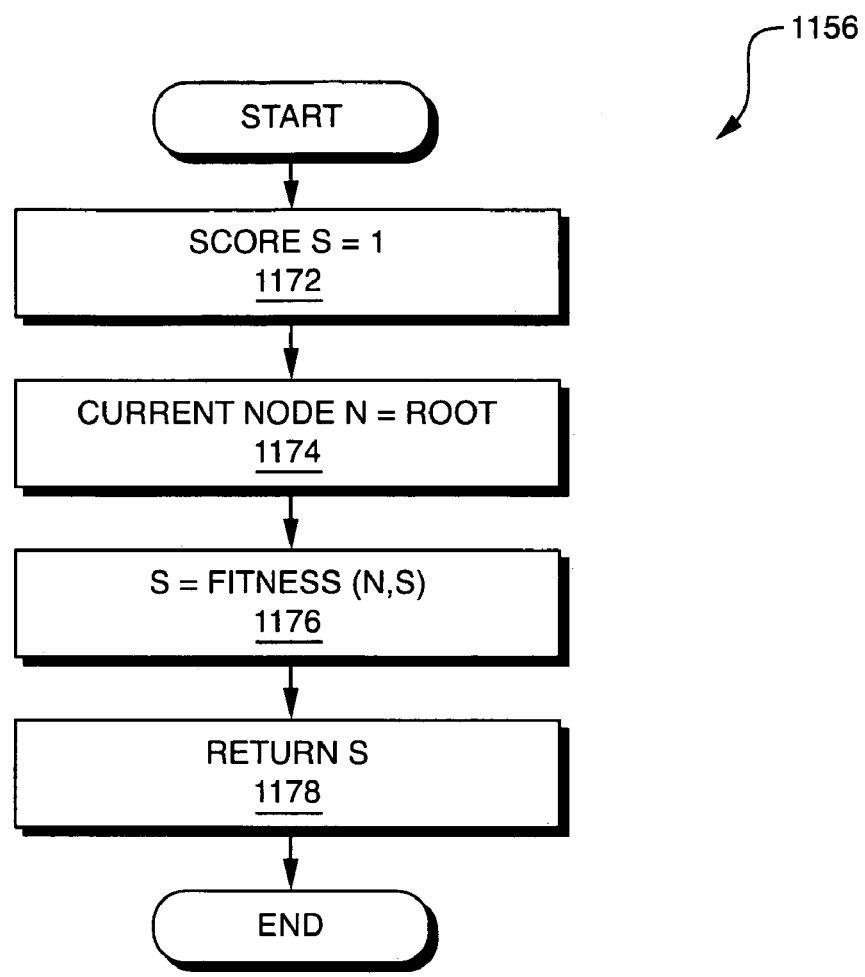
FIGS. 11C-11D are flowcharts of methods that are performed in one embodiment of the present invention to calculate a fitness score for a candidate document.

Referring to FIG. 11C, a flowchart is shown of a method that is performed in one embodiment of the present invention to calculate a fitness score for a candidate document, and which may therefore be used to implement step 1156 of the method 1150 illustrated in FIG. 11B. A fitness score S is initialized to a value of one for the candidate structured document being evaluated (step 1172). The method assigns a current node pointer N to point to the root node in the candidate path corresponding to the candidate document (step 1174).

The method calls a function named Fitness( ) with the values N and S (step 1176) and returns the result as the fitness score for the candidate document (step 1178). As will now be described in more detail, the Fitness( ) function generates the fitness score S using a hierarchical factorization by traversing the candidate path corresponding to the candidate document.

Figure 11D:
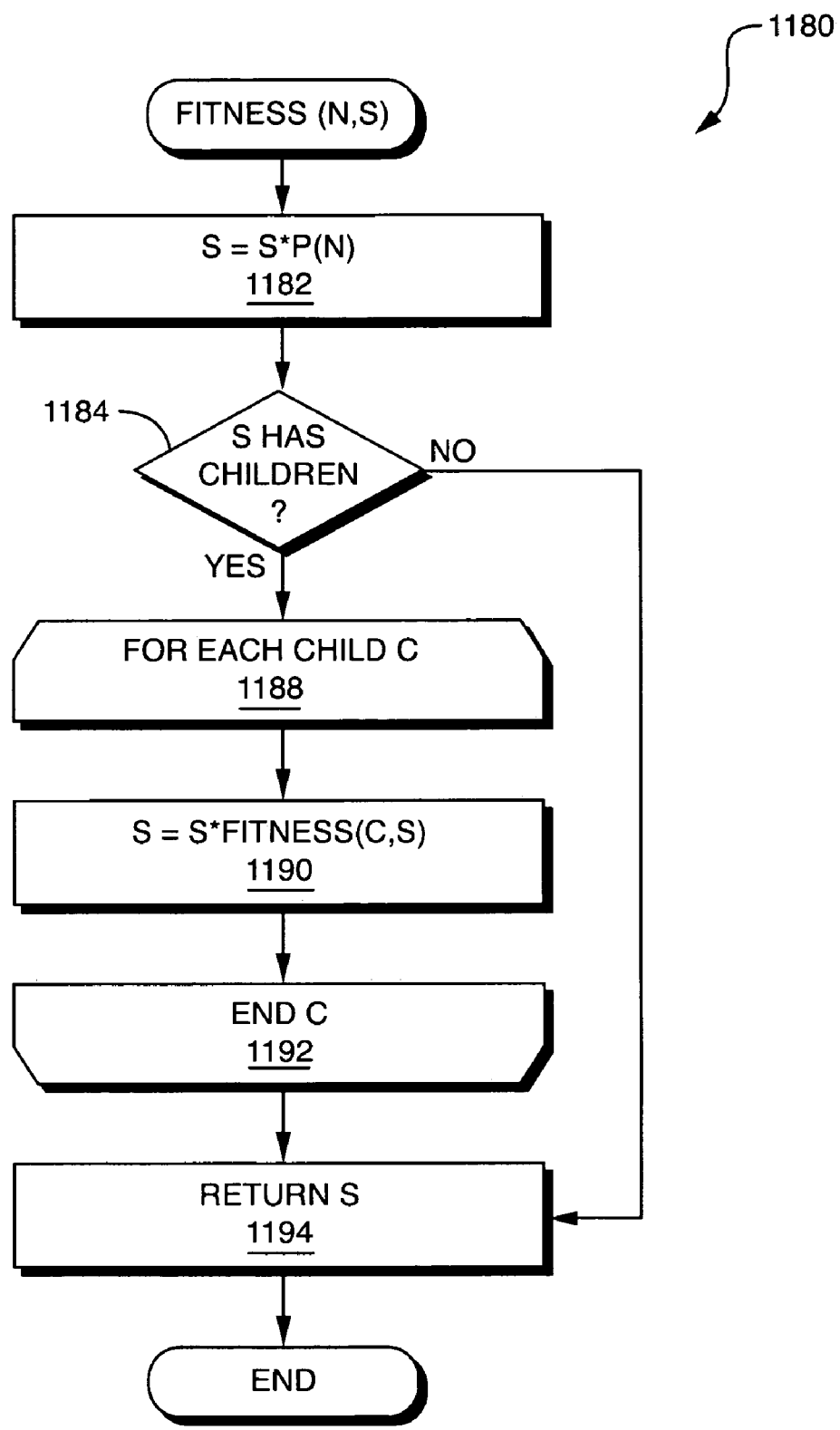

Referring to FIG. 11D, a flowchart is shown of the Fitness( ) function 1180 according to one embodiment of the present invention. The function 1180 identifies the probability P(W (N)) that the text W corresponding to the current node N has been recognized by the language model associated with that node, and multiplies the probability by the current value of S to produce a new value for S (step 1184).

If node N has no children (step 1186), the value of S is returned (step 1194). If node N has children, then the Fitness( ) function 1180 is called recursively on each of the child nodes, with the results being multiplied by the value of S to produce new values of S (steps 1188-1192). The resulting value of S is returned (step 1194).

Upon completion of the method illustrated in FIG. 11C, the value of S represents a fitness score for the entire candidate structured document, and the value of S is returned, e.g., for use in the method 1150 illustrated in FIG. 11B (step 1194).

For example, recall again the text "CT scan of the chest without contrast april twenty second two thousand three". The fitness score (probability) of this text may be obtained by identifying the probability of the text "CT scan of the chest without contrast <DATE>", where <DATE> denotes any date, multiplied by the conditional probability of the text "april twenty second two thousand three" occurring given that the text represents a date.

More generally, the effect of the method illustrated in FIG. 11C is to hierarchically factor probabilities of word sequences according to the hierarchy of the language model 304, allowing the individual probability estimates associated with each language model node to be seamlessly combined with the probability estimates associated with other nodes. This probabilistic framework allows the system to model and use statistical language models with embedded probabilistic finite state grammars and finite state grammars with embedded statistical language models.

As described above, nodes in the language model 304 represent language sub-models which specify the probabilities of occurrence of sequences of words in the spoken audio stream 302. In the preceding discussion, it has been assumed that the probabilities have already been assigned in such language models. Examples of techniques will now be disclosed for assigning probabilities to the language sub-models (such as n-gram language models and context-free grammars) in the language model 304.

Figure 13:
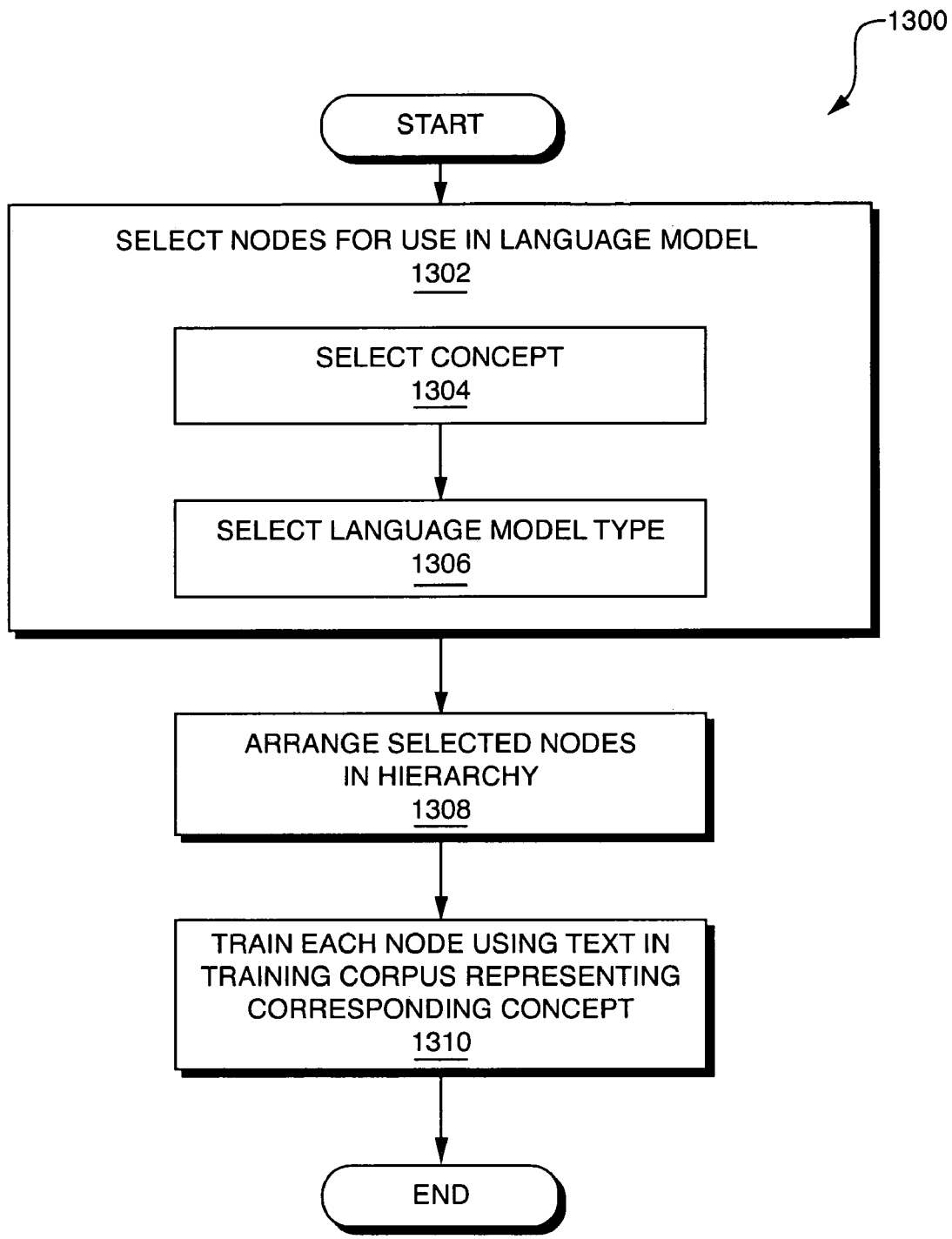
FIG. 13 is a flowchart of a method that is used in one embodiment of the present invention to generate a hierarchical language model for use in generating structured textual documents.

Referring to FIG. 13, a flowchart is shown of a method 1300 that is used in one embodiment of the present invention to generate the language model 304. A plurality of nodes are selected for use in the language model (step 1302). The nodes may, for example, be selected by a transcriptionist or other person skilled in the relevant domain. The nodes may be selected in an attempt to capture all of the types of concepts that may occur in the spoken audio stream 302. For example, in the medical domain, nodes (such as those shown in FIG. 10A) may be selected which represent the sections of a medical report and the concepts (such as dates, times, medications, allergies, vital signs and medical codes) which are expected to occur in a medical report.

A concept and language model type may be assigned to each of the nodes selected in step 1302 (steps 1304-1306). For example, node 306*b* (FIG. 10A) may be assigned the concept "comparison section cue" and be assigned the language model type "finite state grammar." Similarly, node 1006*a* may be assigned the concept "comparison content" and the language model type "n-gram language model."

The nodes selected in step 1302 may be arranged into a hierarchical structure (step 1308). For example, the nodes 1002, 306*a-e*, 1006*a-e*, and 1010 may be arranged into the hierarchical structure illustrated in FIG. 10A to represent and enforce structural dependencies between the nodes.

Each of the nodes selected in step 1302 may then be trained using text representing a corresponding concept (step 1310). For example, a set of training documents may be identified. The set of training documents may, for example, be a set of existing medical reports or other documents in the same domain as the spoken audio stream 302. The training documents may be marked up manually to indicate the existence and location of structures in the document, such as sections, sub-sections, dates, times, codes, and other concepts. Such markup may, for example, be performed automatically on formatted documents, or manually by a transcriptionist or other person skilled in the relevant domain. Examples of techniques for training the nodes selected in step 1302 are described in the above-referenced patent application entitled "Document Transcription System Training."

Conventional language model training techniques may be used in step 1310 to train concept-specific language models for each of the concepts that is marked up in the training documents. For example, the text from all of the marked-up "header" sections in the training documents may be used to train the language model node 306*a* representing the header section. In this way, language models for each of the nodes 1002, 306*a-e*, 1006*a-e*, and 1010 in the language model 304 illustrated in FIG. 10A may be trained. The result of the method 1300 illustrated in FIG. 13 is a hierarchical language model having trained probabilities, which can be used to generate the structured textual document 310 in the manner described above. This hierarchical language model may then be used, for example, to iteratively re-segment the training text, such as by using the techniques disclosed above in conjunction with FIGS. 11B and 12B. The resegmented training text may be used to retrain the hierarchical language model. This process of re-segmenting and re-training may be performed iteratively to repeatedly improve the quality of the language model.

In the examples described above, the structured document generator 308 both recognizes the spoken audio stream 302 and generates the structured textual document 310 using an integrated process, within generating an intermediate non-structured transcript. Such techniques, however, are disclosed merely for purposes of example and do not constitute limitations of the present invention.

Figure 14:
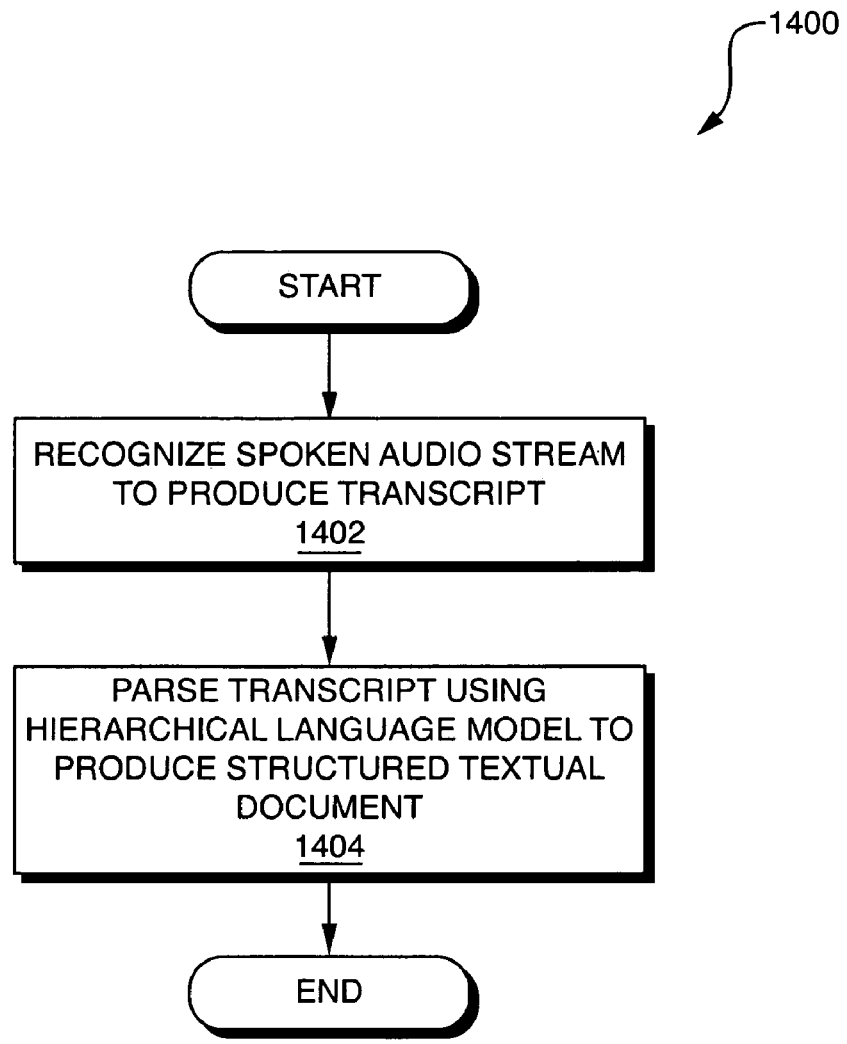
FIG. 14 is a flowchart of a method that is used in one embodiment of the present invention to generate a structured textual document using distinct speech recognition and structural parsing steps.
Figure 15:
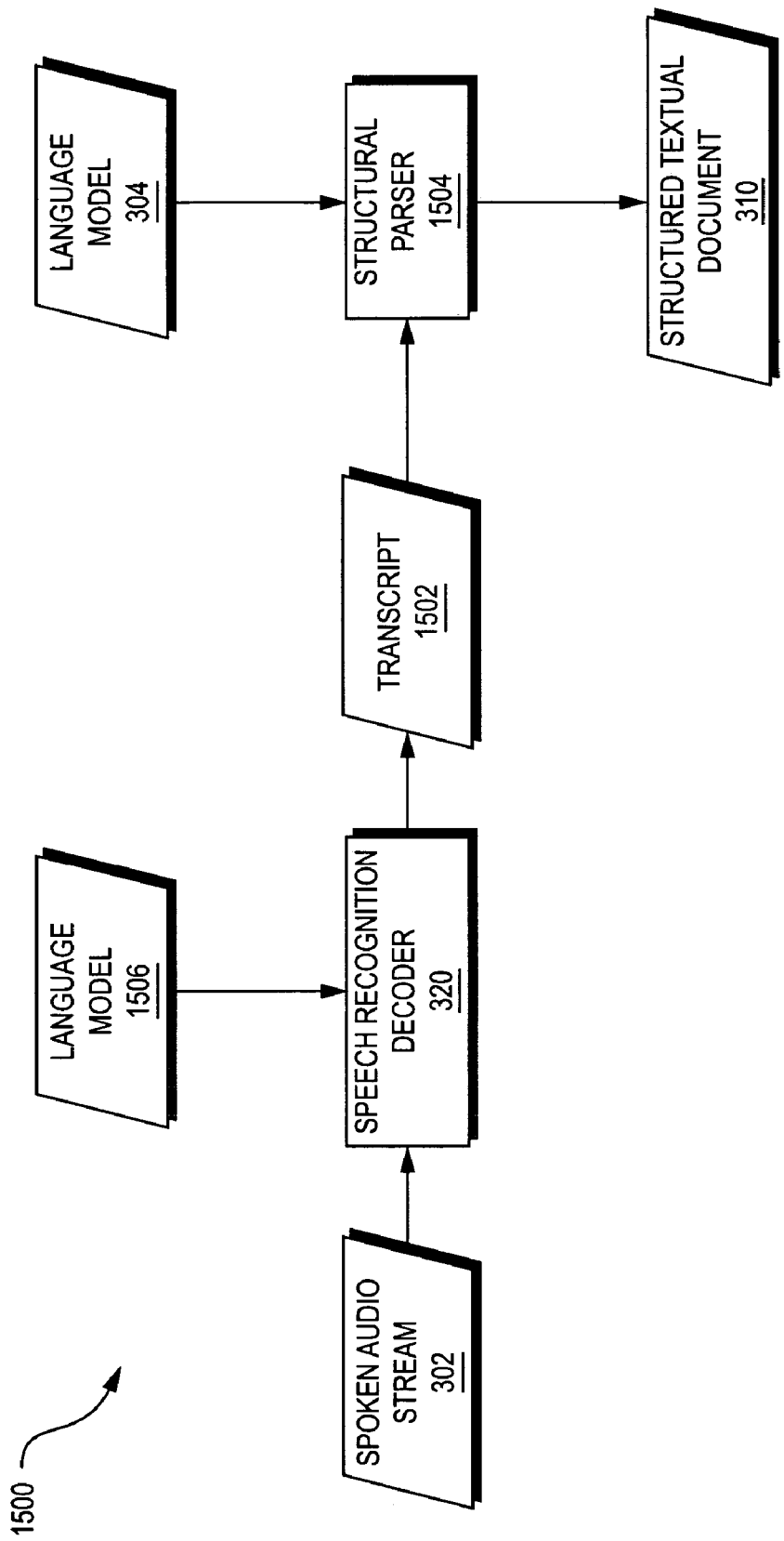
FIG. 15 is a dataflow diagram of a system that performs the method of FIG. 14 according to one embodiment of the present invention.

Referring to FIG. 14, a flowchart is shown of a method 1400 that is used in another embodiment of the present invention to generate the structured textual document 310 using distinct speech recognition and structural parsing steps. Referring to FIG. 15, a dataflow diagram is shown of a system 1500 that performs the method 1400 of FIG. 14 according to one embodiment of the present invention.

The speech recognition decoder 320 recognizes the spoken audio stream 302 using a language model 1506 to produce a transcript 1502 of the spoken audio stream 302. Note that the language model 1506 may be a conventional language model that is distinct from the language model 304. More specifically, the language model 1506 may be a conventional monolithic language model. The language model 1506 may, for example, be generated using the same training corpus as is used to train the language model 304. While portions of the training corpus may be used to train nodes of the language model 304, the entire corpus may be used to train the language model 1506. The speech recognition decoder 320 may, therefore, use conventional speech recognition techniques to recognize the spoken audio stream 302 using the language model 1506 and thereby to produce the transcript 1502.

Note that the transcript 1502 may be a "flat" transcript 1502 of the spoken audio stream 302, rather than a structured document as in the previous examples disclosed above. The transcript 1502 may, for example, include a sequence of flat text resembling the text illustrated in FIG. 4 (which illustrates the spoken audio stream 302 in textual form).

The system 1500 also includes a structural parser 1504, which uses the hierarchical language model 304 to parse the transcript 1502 and thereby to produce the structured textual document 310 (step 1404). The structural parser 1504 may use the techniques disclosed above with respect to FIGS. 11C and 12B to: (1) produce multiple candidate structured documents having the same content as the transcript 1502 but having structures corresponding to different paths through the language model 304; (2) generate fitness scores for each of the candidate structured documents; and (3) select the candidate structured document having the highest fitness score as the final structured textual document. In contrast to the techniques disclosed above with respect to FIGS. 11C and 12B, however, step 1404 may be performed without performing speech recognition to generate each of the candidate structured documents. Rather, once the transcript 1502 has been produced using the speech recognition decoder 320, candidate structured documents may be generated based on the transcript 1502 without performing additional speech recognition.

Figure 10C:
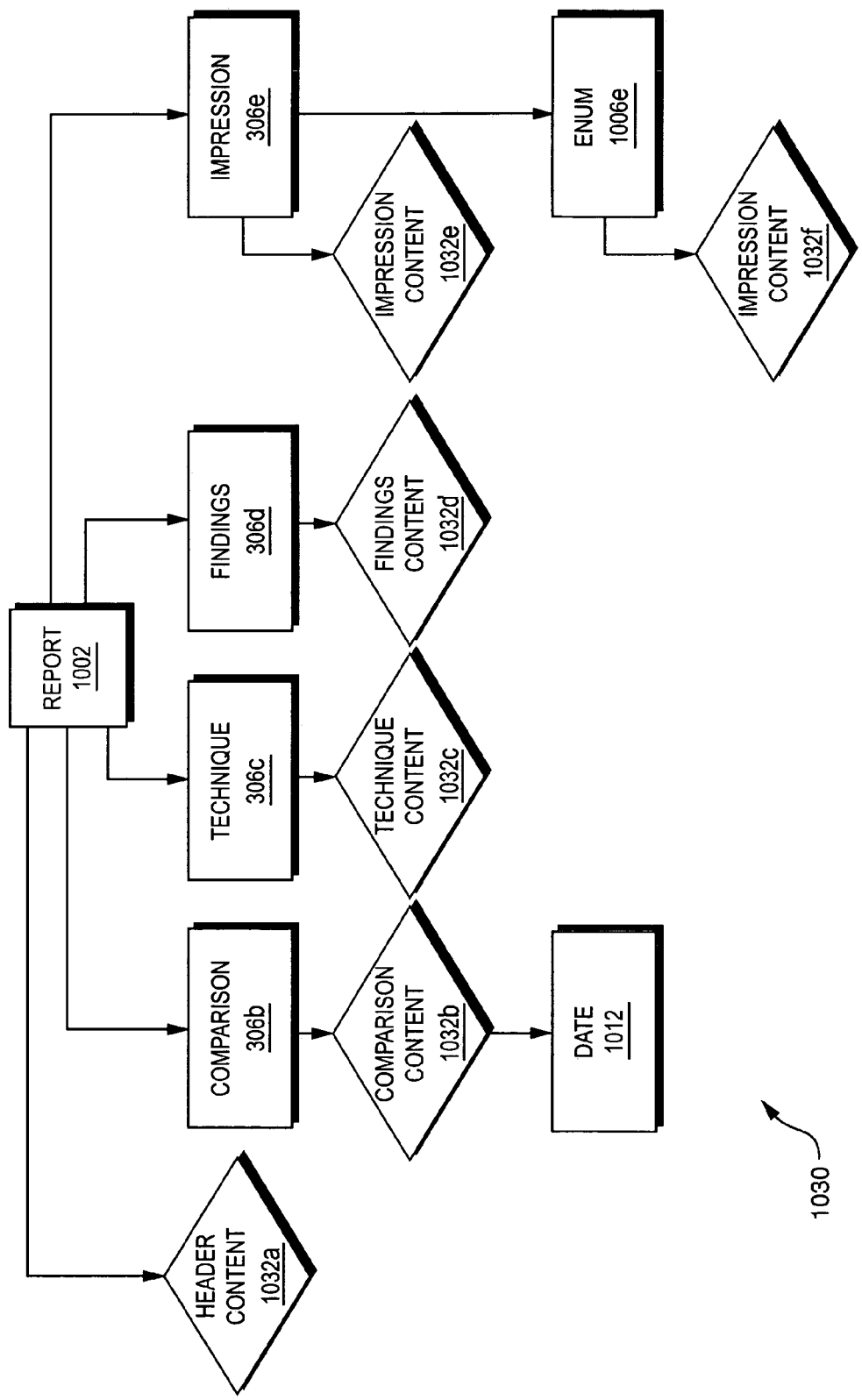
FIG. 10C is a diagram illustrating a hierarchical language model according to another embodiment of the present invention.

Furthermore, the structural parser 1504 need not use the full language model 304 to produce the structured textual document 310. Rather, the structural parser 1504 may use a scaled-down "skeletal" language model, such as the language model 1030 illustrated in FIG. 10C. Note that the example language model 1030 shown in FIG. 10C is the same as the language model 304 shown in FIG. 10A, except that in the skeletal language model 1030 the content language model nodes 306*a*, 1006*a-d*, and 1010 have been replaced with universally-accepting language models 1032*a-f*, also referred to as "don't care" language models. The language models 1032*a-f* will accept any text that is provided to them as input. The heading cue language models 306*b-e* in the skeletal language model 1030 enable the structural parser 1504 to parse the transcript 1502 into the correct sub-structures in the structured document 310. The use of the universally-accepting language models 1032*a-f*, however, enables the structural parser 1504 to perform such structural parsing without incurring the (typically significant) expense of training content language models, such as the models 306*a*, 1006*a-d*, and 1010 shown in FIG. 10A.

Note that the skeletal language model 1030 may still include language models, such as the date language model 1012, corresponding to lower-level concepts. As a result, the skeletal language model 1030 may be used to generate the structured document 310 from the transcript 1502 without incurring the overhead of training content language models, while retaining the ability to parse lower-level concepts into the structured document 310.

Among the advantages of the invention are one or more of the following. The techniques disclosed herein replace the traditional global language model with a combination of specialized local language models which are more well-suited to section of a document than a single generic language model. Such a language model has a variety of advantages.

For example, the use of a language model which contains sub-models, each of which corresponds to a particular concept, is advantageous because it allows the most appropriate language model to be used to recognize speech corresponding to each concept. In other words, if each of the sub-models corresponds to a different concept, then each of the sub-models may be used to perform speech recognition on speech representing the corresponding concept. Because the characteristics of speech may vary from concept to concept, the use of such concept-specific language models may produce better recognition results than those which would be produced using a monolithic language model for all concepts.

Although the sub-models of a language model may correspond to sections of a document, this is not a limitation of the present invention. Rather, each sub-model in the language model may correspond to any concept, such as a section, paragraph, sentence, date, time or ICD9 code. As a result, sub-models in the language model may be matched to particular concepts with a higher degree of precision than would be possible if only section-specific language models were employed. The use of such concept-specific language models for a wide variety of concepts may further improve speech recognition accuracy.

Furthermore, hierarchical language models designed in accordance with embodiments of the present invention may have multi-level hierarchical structures, with the effect of nesting sub-models inside of each other. As a result, sub-models in the language model may be applied to portions of the spoken audio stream 302 at various levels of granularity, with the most appropriate language model being applied at each level of granularity. For example, a "header section" language model may be applied generally to speech inside of the header section of a document, while a "date" language model may be applied specifically to speech representing dates in the header section. This ability to nest language models and to apply nested language models to different portions of speech may further improve recognition accuracy by enabling the most appropriate language model to be applied to each portion of a spoken audio stream.

Figure 1A:
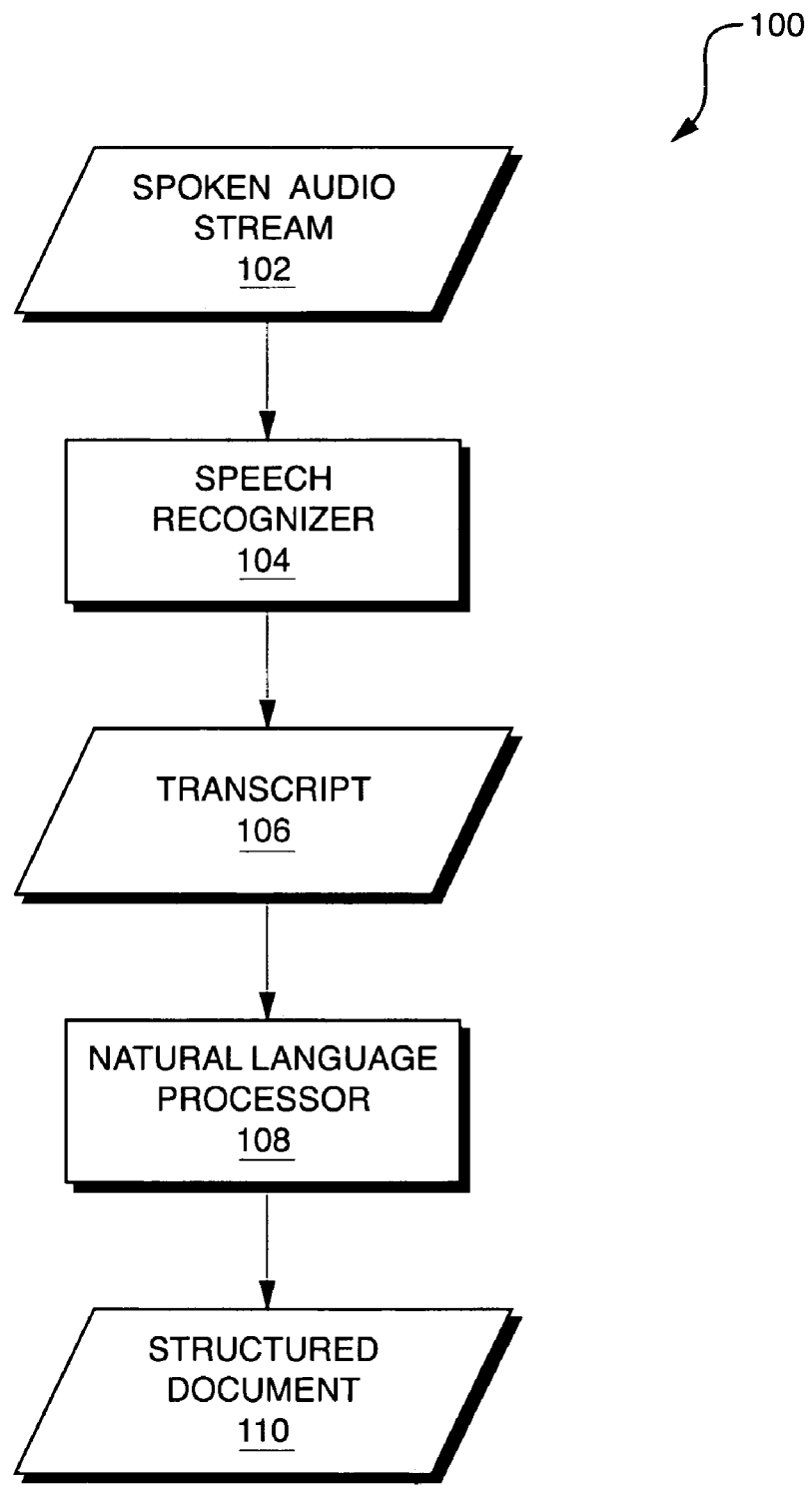
FIG. 1A is a dataflow diagram of a prior art system for generating a structured document based on a spoken audio stream.

Another advantage of using a language model which includes a plurality of sub-models is that the techniques disclosed herein may use such a language model to generate a structured textual document from a spoken audio stream using a single integrated process, rather than the prior art two-step process 100 illustrated in FIG. 1A in which a speech recognition step is followed by a natural language processing step. In the two-step process 100 illustrated in FIG. 1A the steps performed by the speech recognizer 104 and the natural language processor 108 are completely decoupled. Because the automatic speech recognizer 104 and natural language processor 108 operate independently from each other, the output 106 of the automatic speech recognizer 104 is a literal transcript of the spoken content in the audio stream 102. The literal transcript 106 therefore contains text corresponding to all spoken utterances in the audio stream 102, whether or not such utterances are relevant to the final desired structured textual document. Such utterances may include, for example, hesitations, extraneous words or repetitions, as well as structural hints or task-related words. Furthermore, the natural language processor 108 relies on the successful detection and transcription of certain key words and/or key phrases, such as structural hints. If these key words/phrases are misrecognized by the automatic speech recognizer 104, the identification of structural entities by the natural language processor 108 may be negatively affected. In contrast, in the method 200 illustrated in FIG. 2, speech recognition and natural language processing are integrated, thereby enabling the language model to influence both the recognition of words in the audio stream 302 and the generation of structure in the structured textual document 310, thereby improving the overall quality of the structured document 310.

In addition to generating the structured document 310, the techniques disclosed herein may also be used to extract and interpret semantic content from the audio stream 302. For example, the date language model 1012 (FIGS. 10A-10B) may be used to identify portions of the audio stream 302 that represent dates, and to store representations of such dates in a computer-readable form. For example, the techniques disclosed herein may be used to identify the spoken phrase "october first nineteen ninety three" as a date and to store the date in a computer-readable form, such as "month=10, day=1, year=1998". Storing such concepts in a computer-readable form allows the content of such concepts to be easily processed by a computer, such as by sorting document sections by date or identifying medications prescribed prior to a given date. Furthermore, the techniques disclosed herein enable the user to define different portions (e.g., sections) of the document, and to choose which concepts are to be extracted in each section. The techniques disclosed herein, therefore, facilitate the recognition and processing of semantic content in spoken audio streams. Such techniques may be applied instead of or in addition to storing extracted information in a structured document.

Domains, such as the medical and legal domains, in which there are large bodies of pre-existing recorded audio streams to use as training text, may find particular benefit in techniques disclosed herein. Such training text may be used to train the language model 304 using the techniques disclosed above with respect to FIG. 13. Because documents in such domains may be required to have well-defined structures, and because such structures may be readily identifiable in existing documents, it may be relatively easy (albeit time-consuming) to correctly identify the portions of such existing documents to use in training each of the concept-specific language model nodes in the language model 304. As a result, each of the language model nodes may be well-trained to recognize the corresponding concept, thereby increasing recognition accuracy and increasing the ability of the system to generate documents having the required structure.

Furthermore, techniques disclosed herein may be applied within such domains without requiring any changes in the existing process by which audio is recorded and transcribed. In the medical domain, for example, doctors may continue to dictate medical reports in their current manner. The techniques disclosed herein may be used to generate documents having the desired structure regardless of the manner in which the spoken audio stream is dictated. Alternative techniques requiring changes in workflow, such as techniques which require speakers to enroll (by reading training text), which require speakers to modify their manner of speaking (such as by always speaking particular concepts using predetermined spoken forms), or which require transcripts to be generated in a particular format, may be prohibitively costly to implement in domains such as the medical and legal domains. Such changes might, in fact, be inconsistent with institutional or legal requirements related to report structure (such as those imposed by insurance reporting requirements). The techniques disclosed herein, in contrast, allow the audio stream 302 to be generated in any manner and to have any form.

Additionally, individual sub-models 306a-e in the language model 304 may be updated easily without affecting the remainder of the language model. For example, the header content 306a sub-model may be replaced with a different header content sub-model which accounts differently for the way in which the document header is dictated. The modular structure of the language model 304 enables such modification/replacement of sub-models to be performed without the need to modify any other part of the language model 304. As a result, parts of the language model 304 may easily be updated to reflect different document dictation conventions.

Furthermore, the structured textual document 310 that is produced by various embodiments of the present invention may be used to train a language model. For example, the training techniques described in the above-referenced patent application entitled "Document Transcription System Training" may use the structured textual document 310 to retrain and thereby improve the language model 304. The retrained language model 304 may then be used to produce subsequent structured textual documents, which may in turn be used to retrain the language model 304. This iterative process may be employed to improve the quality of the structured documents that are produced over time.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

The spoken audio stream 302 may be any audio stream, such as a live audio stream received directly or indirectly (such as over a telephone or IP connection), or an audio stream recorded on any medium and in any format. In distributed speech recognition (DSR), a client performs preprocessing on an audio stream to produce a processed audio stream that is transmitted to a server, which performs speech recognition on the processed audio stream. The audio stream 302 may, for example, be a processed audio stream produced by a DSR client.

Although in the examples above each node in the language model 304 is described as containing a language model that corresponds to a particular concept, this is not a requirement of the present invention. For example, a node may include a language model that results from interpolating a concept-specific language model associated with the node with one or more of: (1) global background language models, or (2) concept-specific language models associated with other nodes.

In the examples above, a distinction may be made between "grammars" and "text." It should be appreciated that text may be represented as a grammar, in which there is a single spoken form having a probability of one. Therefore, documents which are described herein as including both text and grammars may be implemented solely using grammars if desired. Furthermore, a finite state grammar is merely one kind of context-free grammar, which is a kind of language model that allows multiple alternative spoken forms of a concept to be represented. Therefore, any description herein of techniques that are applied to finite state grammars may be applied more generally to any other kind of grammar. Furthermore, although the description above may refer to finite state grammars and n-gram language models, these are merely examples of kinds of language models that may be used in conjunction with embodiments of the present invention. Embodiments of the present invention are not limited to use in conjunction with any particular kind(s) of language model(s).

The invention is not limited to any of the described fields (such as medical and legal reports), but generally applies to any kind of structured documents.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMS. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A computer-implemented method comprising steps of:
(A) identifying a probabilistic language model including a plurality of probabilistic language models associated with a plurality of concepts logically organized in a first hierarchy;
(B) using a speech recognition decoder to apply the probabilistic language model to a spoken audio stream to produce a document including content organized into a plurality of sub-structures logically organized in a second hierarchy having a logical structure defined by a path through the first hierarchy, comprising:
(B)(1) identifying a path through the first hierarchy, comprising:
(B)(1)(a) identifying a plurality of paths through the first hierarchy;
(B)(1)(b) for each of the plurality of paths P, producing a candidate structured document for the spoken audio stream by using the speech recognition decoder to recognize the spoken audio stream using the language models on path P;

(B)(1)(c) applying a metric to the plurality of candidate structured documents produced in step (B)(1)(b) to produce a plurality of fitness scores for the plurality of candidate structured documents; and (B)(1)(d) selecting the path which produces the candidate structured document having the highest fitness score;

(B)(2) generating a document having a structure corresponding to the path identified in step (B)(1).

2. The method of claim 1, wherein the step (B)(2) comprises a step of traversing the path through the first hierarchy to generate the document.

3. The method of claim 1, wherein the step (B)(1) comprises a step of identifying a path through the first hierarchy which, when applied by a speech recognition decoder to recognize the spoken audio stream, produces an optimal recognition result with respect to the first hierarchy of the plurality of probabilistic language models.

4. The method of claim 1, wherein the plurality of sub-structures includes a sub-structure representing a semantic concept.

5. The method of claim 4, wherein the semantic concept comprises a date.

6. The method of claim 4, wherein the semantic concept comprises a medication.

7. The method of claim 4, wherein the semantic concept is represented in the document in a computer-readable form.

8. The method of claim 1, wherein the plurality of probabilistic language models includes at least one n-gram language model.

9. The method of claim 1, further comprising a step of:
(C) rendering the document to produce a rendition indicating the structure of the document.

10. The method of claim 1, wherein the plurality of probabilistic language models includes at least one finite state language model.

11. The method of claim 10, wherein the plurality of probabilistic language models includes at least one n-gram language model.

12. An apparatus comprising:
identification means for identifying a probabilistic language model including a plurality of probabilistic language models associated with a plurality of concepts logically organized in a first hierarchy; and
document production means for using a speech recognition decoder to apply the probabilistic language model to a spoken audio stream to produce a document including content organized into a plurality of sub-structures logically organized in a second hierarchy having a logical structure defined by a path through the first hierarchy, the document production means comprising:
second identification means for identifying a path through the first hierarchy, comprising:
means for identifying a plurality of paths through the first hierarchy;
candidate production means for producing, for each of the plurality of paths P, a candidate structured document for the spoken audio stream by using the speech recognition decoder to recognize the spoken audio stream using the language models on path P;
means for applying a metric to the plurality of candidate structured documents produced by the candidate production means to produce a plurality of fitness scores for the plurality of candidate structured documents; and
means for selecting the path which produces the candidate structured document having the highest fitness score; and
means for generating a document having a structure corresponding to the path identified by the second identification means.

13. The apparatus of claim 12, wherein the means for generating the document comprises means for traversing the path through the first hierarchy to generate the document.

14. The apparatus of claim 12, wherein the plurality of probabilistic language models includes at least one n-gram language model.

15. The apparatus of claim 12, wherein the plurality of probabilistic language models includes at least one finite state language model.

16. The apparatus of claim 15, wherein the plurality of probabilistic language models includes at least one n-gram language model.

17. The apparatus of claim 12, wherein the plurality of sub-structures includes a sub-structure representing a semantic concept.

18. The apparatus of claim 17, wherein the semantic concept comprises a date.

19. The apparatus of claim 17, wherein the semantic concept comprises a medication.

20. The apparatus of claim 17, wherein the semantic concept is represented in the document in a computer-readable form.

21. The apparatus of claim 12, further comprising:
means for rendering the document to produce a rendition indicating the structure of the document.

* * * * *